(12) United States Patent
Bedos

(10) Patent No.: US 10,918,891 B2
(45) Date of Patent: Feb. 16, 2021

(54) COSMETIC TREATMENT METHOD FOR THE SKIN

(71) Applicant: SYNTIVIA, Toulouse (FR)

(72) Inventor: Philippe Bedos, Donneville (FR)

(73) Assignee: SYNTIVIA, Toulouse (FR)

(*) Notice: Subject to any disclaimer, the term of this patent is extended or adjusted under 35 U.S.C. 154(b) by 0 days.

(21) Appl. No.: 16/318,772

(22) PCT Filed: Jul. 21, 2017

(86) PCT No.: PCT/FR2017/052007
§ 371 (c)(1),
(2) Date: Jan. 18, 2019

(87) PCT Pub. No.: WO2018/015688
PCT Pub. Date: Jan. 25, 2018

(65) Prior Publication Data
US 2019/0240512 A1    Aug. 8, 2019

(30) Foreign Application Priority Data

Jul. 22, 2016 (FR) ...................................... 1657014

(51) Int. Cl.
| | | |
|---|---|---|
| *A61Q 19/08* | (2006.01) | |
| *A61Q 17/04* | (2006.01) | |
| *A61K 8/49* | (2006.01) | |
| A61K 8/64 | (2006.01) | |
| A61K 8/67 | (2006.01) | |

(52) U.S. Cl.
CPC ............ *A61Q 19/08* (2013.01); *A61K 8/4926* (2013.01); *A61Q 17/04* (2013.01); *A61K 8/64* (2013.01); *A61K 8/67* (2013.01); *A61K 2800/28* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 2015/0010484 A1* | 1/2015 | Chiang | .................. A61Q 19/02 424/62 |
| 2015/0031740 A1 | 1/2015 | Bedos et al. | |

FOREIGN PATENT DOCUMENTS

| | | |
|---|---|---|
| DE | 201 10 355 U1 | 8/2001 |
| JP | 2008 239545 A | 10/2008 |
| WO | 2006/005455 A2 | 1/2006 |
| WO | 2013/087834 A2 | 6/2013 |

OTHER PUBLICATIONS

Anonymous: "Vitamin B6—Healthy Skin Depends on this Vitamin", Jul. 10, 2011 (Jul. 10, 2011), XP055328321, Retrieved from the Internet <URL:http://vitamedica.com/wellness-blog/vitamin-b-6/> [retrieved on Dec. 12, 2016].
International Search Report, dated Nov. 10, 2017, from corresponding PCT/FR2017/052007 application.

* cited by examiner

*Primary Examiner* — Brian J Davis
(74) *Attorney, Agent, or Firm* — Nixon & Vanderhye

(57) ABSTRACT

Disclosed is a cosmetic treatment method for the skin, in particular for preventing and/or repairing the signs of skin ageing, that includes administering, and in particular applying topically to the skin, a composition containing, in a cosmetically acceptable vehicle, a compound of general formula (I): (formula I) in which $R_1$, $R_2$, $R_3$, $R_4$, $R_5$, $R_6$, $R_7$ and $R_8$, which may be identical or different, each represent a hydrogen atom, a halogen atom, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one group from $R_1$, $R_2$, $R_3$, $R_4$, $R_5$, $R_6$, $R_7$ and $R_8$ not representing a hydrogen atom or a halogen atom, Z represents a covalent bond or a spacer arm, or one of the salts of same.

17 Claims, 3 Drawing Sheets

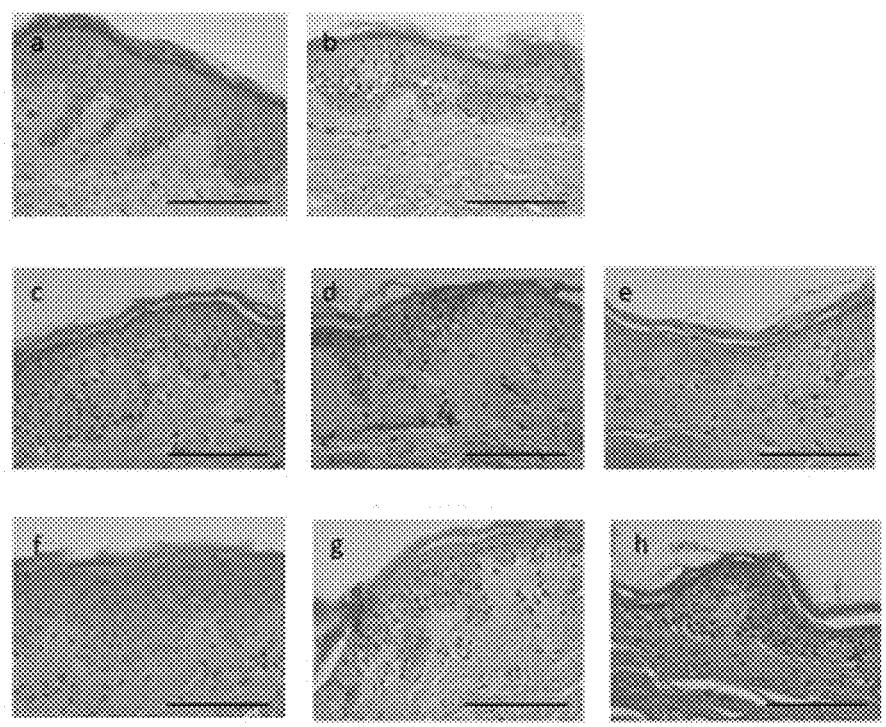
FIG 5
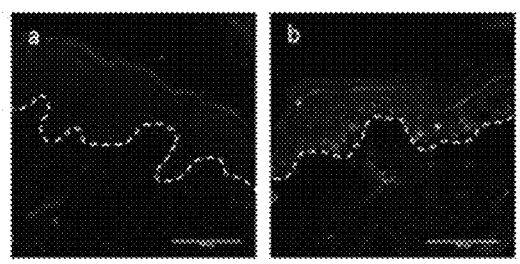
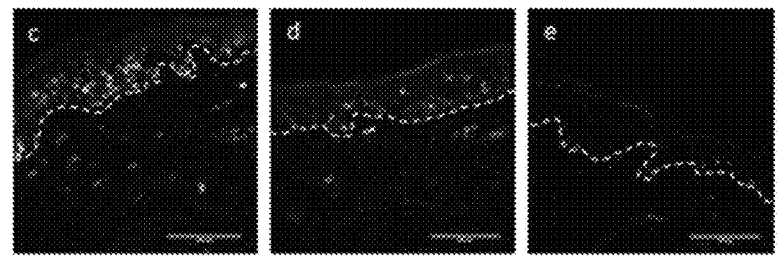
FIG 6
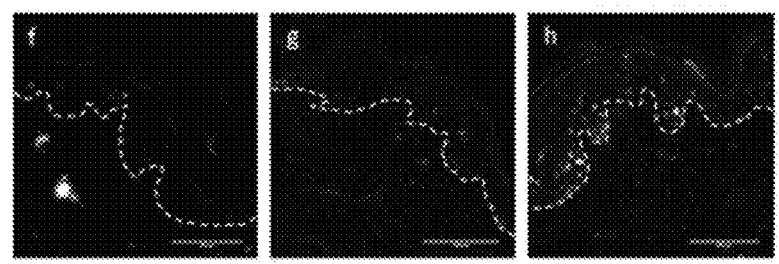

COSMETIC TREATMENT METHOD FOR THE SKIN

The present invention lies in the field of cosmetic compositions, in particular for topical use, intended for the protection and/or the treatment of the skin, in particular in order to prevent and/or repair the effects of skin ageing, in particular related to external aggressions. More particularly, the present invention relates to a method for cosmetic treatment of the skin implementing a compound satisfying a specific general formula, as well as the cosmetic use of such a compound, and a cosmetic composition containing such a compound.

The skin is the first barrier protecting the body against external aggressions. The phenomenon of skin ageing, whether natural or caused by these external aggressions, weakens this barrier function. In particular, exposition to external aggressions makes the skin fragile and induces a plurality of processes of degeneration that accelerate skin ageing, in particular: inflammatory reactions, the activation of the production of free radicals, harmful for skin metabolism, the stimulation of enzymes that attack the skin in depth, such as matrix metalloproteases (MMP), the damage to DNA induced by ultraviolet radiation, which leads to genome instability and can lead to the premature death of the cells, etc.

These external aggressions include in particular the aggressions by ultraviolet radiation, exposure to pollutants, such as heavy metals, cigarette smoke, etc.

The symptoms of skin ageing are in particular the appearance of wrinkles, dryness, roughness, thinning and the loss of elasticity of the skin. The treatment of these symptoms has become a major issue for the cosmetic industry.

Knowledge of the physiology of the skin has allowed to propose cosmetic solutions to various disorders induced by external aggressions. The prior art has thus proposed various cosmetic compositions, containing active principles of various types, in order to prevent and repair the effects of ageing of the skin.

The cosmetic active principles proposed by the prior art in order to improve the appearance of the skin include for example the compounds of plant origin such as the polyphenols, the antioxidant activity of which has been used to prevent oxidative stress in the skin, via trapping of the free radicals resulting from external aggressions, for example from exposure of the skin to ultraviolet rays (UV). Caffeic acid is an example of such a polyphenol implemented in cosmetic compositions qualified as anti-ageing proposed by the prior art, for example illustrated by the document JP 2008/239545. The cosmetic compositions containing such antioxidant compounds allow, to a certain extent, to slow down the appearance of the symptoms of ageing. Their effectiveness is, however, limited, in particular with regard to certain types of external aggressions.

The present invention aims to propose a method for cosmetic treatment of the skin, implementing a composition for topical use, that allows to effectively protect and/or repair the skin with regard to the effects of skin ageing related to external aggressions.

It has now been discovered by the present inventors that a certain class of compounds, satisfying a specific general formula, allow, implemented as active principles in cosmetic compositions, in particular for topical use, to achieve such a result, and in particular to effectively protect the skin against external aggressions.

Thus, according to a first aspect, the present invention relates to a method for non-therapeutic, cosmetic treatment of the skin of an individual, in particular in order to prevent and/or repair the effects of ageing of the skin, in particular caused by external aggressions. This method involves the administration, to said individual, of a composition containing, in a cosmetically acceptable vehicle, a compound having the general formula (I):

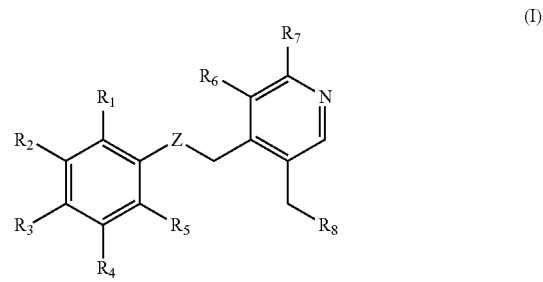

wherein:

$R_1$, $R_2$, $R_3$, $R_4$, $R_5$, $R_6$, $R_7$ and $R_8$, which may be identical or different, each represent a hydrogen atom, a halogen atom, such as an atom of fluorine, of chlorine, of bromine or of iodine, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one group out of $R_1$, $R_2$, $R_3$, $R_4$, $R_5$, $R_6$, $R_7$ and $R_8$ not representing a hydrogen atom or a halogen atom, Z represents a covalent bond or a spacer arm, or one of the salts thereof.

The general formula (I), as well as all the formulas presented below, encompass all the possible combinations of isomer forms at the asymmetrical carbons, and all the mixtures of such isomer forms. Starting from a mixture of isomers, each specific isomer can be obtained by purification methods conventional per se for a person skilled in the art.

The expression "cosmetically acceptable vehicle" means in particular in the present description, in a manner conventional per se, that the vehicle is adapted to a use by contact with human and animal cells, in particular the cells of the skin. Preferably, this vehicle has an odour, a colour and a touch that are pleasant, it does not generate unacceptable discomfort likely to turn a user away from the composition.

Preferably, in the general formula (I), $R_3$ does not represent a hydrogen atom and $R_1$ and $R_5$ each represent a hydrogen atom.

At least one substituent out of $R_2$, $R_3$ and $R_4$ preferably represents a hydroxyl group.

In particularly preferred modes of implementation of the invention, the administration of the composition to the individual is carried out by applying the composition topically onto the skin of the individual.

Otherwise, the administration of the composition to the individual can in particular be carried out orally, the present invention then lying in the field of nutraceuticals. The composition according to the invention for cosmetic treatment of the skin is then in the form of a food supplement, the cosmetically acceptable vehicle being a vehicle suitable for oral administration to humans.

The method for non-therapeutic cosmetic treatment according to the invention advantageously allows to prevent and/or repair in a particularly effective manner the signs of ageing in the skin, via administration, in particular via topical application, of the composition containing a compound having the general formula (I) above onto the skin of an individual, in particular onto a zone of healthy skin, in particular not affected by an inflammatory disease.

This compound having the general formula (I) allows in particular, and in a particularly effective manner, to protect the skin against double-strand breaks of the DNA induced by external aggressions such as ultraviolet rays, in particular, in an entirely surprising manner, by UVAs, or exposure to cigarettes. It allows in particular to:

protect the skin from the oxidative stress induced by ultraviolet rays, more particularly to preserve the integrity of the skin cells exposed to ultraviolet radiation and to limit their ageing caused by the overexpression of the free radicals. At a low concentration, the compound implemented in the method according to the invention reduces, in particular up to 40%, the generation of hydrogen peroxide in the keratinocytes subjected to UV stress;

protect the skin from the polluting stress induced by the heavy metals, in particular cadmium;

protect the skin from the polluting stress induced by cigarette smoke, known in particular for being an aggression that causes double-strand breaks of the DNA;

in a more general manner, protect and regenerate the skin in depth. The method according to the invention thus allows to protect and repair the epidermal barrier, and to preserve the structure of the dermis, despite the exposure to external aggressions.

The compound implemented in the method according to the invention further has a soothing effect, in particular via inhibition of the expression of the cytokines secreted during one of the initial inflammatory responses of the skin, such as Interleukin 8 (IL8) and tumour necrosis factor (TNFα). In particular, the compound implemented in the method according to the invention reduces the expression of the genes of the IL8 and of the TNFα by the keratinocytes by 75% and 45%, respectively, even at a low concentration. It inhibits, up to 30%, the production of IL8 in keratinocytes subjected to the inflammation in the presence of interleukin IL1β.

It has been demonstrated by the present inventors that these effects of protection/repair of the skin, in particular in relation to the signs of ageing, occur in particular, but not in a limiting manner, via the following effects of the compound implemented in the method according to the invention: induction of the overexpression of certain genes of the cells of the skin coding for proteins having an anti-ageing effect on the skin, and inhibition of the expression of other genes coding for proteins causing symptoms of ageing. The action of this compound according to the invention is expressed in particular by a reinforcement of the barrier function of the skin, the induction of the neosynthesis of essential proteins of the extracellular matrix of the skin, and the activation of proteins that are regenerative or detoxifying in the skin.

More particularly, but not in a limiting manner, it has been demonstrated by the present inventors that the compound implemented in the method according to the invention has the following effects:

an effect of protection of the proteins of the extracellular matrix of the skin (ECM), via inhibition of the expression of the matrix metalloproteases (MMP) by the keratinocytes. The matrix metalloproteases, in particular MMP3, degrade numerous components of the extracellular matrix of the skin, in particular fibronectin, laminin, collagens, and proteoglycans. The compound implemented in the method according to the invention inhibits, in particular up to 50%, the expression of MMP3 by the keratinocytes, and, up to 75%, the expression of MMP9, another matrix metalloprotease responsible in particular for the degradation of collagens;

an effect of promoting the repair of the DNA, in particular by stimulation of the gene of the Sirtuin-6 in the fibroblasts. Located in the nucleus of the cell and associated with chromatin, this Sirtuin participates in the general preservation of the stability of the genome, and is involved in the repair of double-strand breaks, in repair by base excisions, and in the protection of the telomers. The compound implemented in the method according to the invention stimulates, up to 13%, the protein expression of the Sirtuin-6, which turns out to be particularly significant.

The compound according to the invention turns out to be in particular more effective, in terms of protection/repair of the skin with regard to external aggressions, in particular by cigarette extract, or exposure to ultraviolet radiation, in particular to UVAs, then the antioxidant agent known from the prior art constituted by caffeic acid, having the formula:

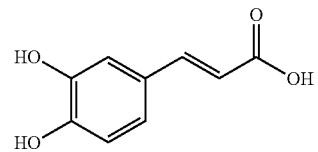 [SMILES: O=C(O)/C=C/c1ccc(O)c(O)c1]

and this in a completely unexpected manner.

It likewise turns out to be much more effective than pyridoxamine, having the formula:

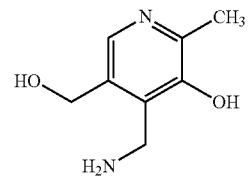

In specific modes of implementation of the method according to the invention, in the general formula (I), Z represents a spacer arm carrying an amide function.

In the general formula (I), Z can in particular represent a group having the formula (II):

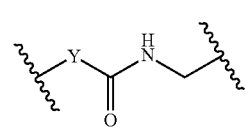

(II)

wherein Y represents a covalent bond or a linear or branched, saturated or unsaturated, C1-C16 hydrocarbon radical, preferably a C2-C4 alkenyl radical, and preferably a C2 alkenyl radical.

Preferably, in the general formula (I), at least one out of $R_3$, $R_4$, $R_5$, $R_6$ and $R_5$ represents a hydroxyl group, and Y represents a covalent bond or a C2-C4 alkenyl radical.

The method according to the invention can in particular implement a compound of general formula (I) having the more specific formula (I'):

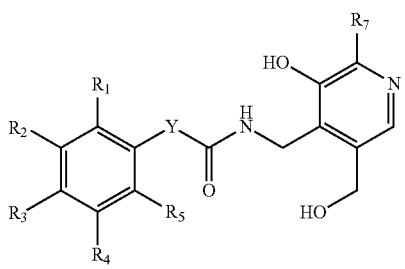

(I')

wherein

R$_1$, R$_2$, R$_3$, R$_4$, R$_5$ and R$_7$, which may be identical or different, each represent a hydrogen atom, a halogen atom, such as an atom of fluorine, of chlorine, of bromine or of iodine, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one group out of R$_1$, R$_2$, R$_3$, R$_4$ and R$_5$ representing a hydroxyl group, and Y represents a covalent bond or a C2-C4, preferably C2, alkenyl radical.

Preferably, in the general formula (I'), at least R$_1$ and R$_2$ each represent a hydrogen atom.

In specific modes of implementation of the invention, in the formula (I'), R$_3$ does not represent a hydrogen atom and R$_1$ and R$_5$ each represent a hydrogen atom.

Preferably, in the formula (I'), at least one substituent out of R$_2$, R$_3$ and R$_4$ represents a hydroxyl group.

In specific modes of implementation of the invention, the method for cosmetic treatment of the skin implements a compound of general formula (I), having the more specific formula (I"):

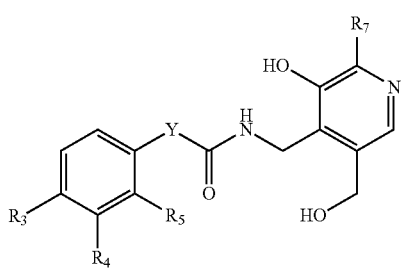

(I")

wherein:

R$_3$, R$_4$, R$_5$ each represent a hydrogen atom, a halogen atom, such as an atom of fluorine, of chlorine, of bromine or of iodine, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one first group out of R$_3$, R$_4$ and R$_5$ representing a hydroxyl group, and at least one second group out of R$_3$, R$_4$ and R$_5$ representing a hydroxyl group or an —OR' radical in which R' represents a linear or branched, saturated or unsaturated, C1-C4, preferably C1, hydrocarbon radical, R$_7$ represents a linear or branched, saturated or unsaturated, C1-C4, preferably C1, hydrocarbon radical, and Y represents a covalent bond or a C2-C4 alkenyl radical, preferably a C2 alkenyl radical.

Preferably, in the formula (I"), R$_3$ does not represent a hydrogen atom and R$_5$ represents a hydrogen atom.

In the formula (I"), at least one substituent out of R$_3$ and R$_4$ represents preferably a hydroxyl group.

In specific modes of implementation of the invention, the method for cosmetic treatment of the skin implements a compound satisfying the formula

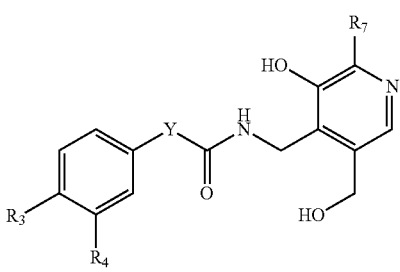

(I''')

wherein

R$_3$ represents a hydroxyl group, or an —OR' radical in which R' represents a linear or branched, saturated or unsaturated, C1-C16 hydrocarbon radical, preferably a methyl group, R$_4$ represents a hydrogen atom or a hydroxyl group, and R$_7$ represents a linear or branched, saturated or unsaturated, C1-C4 hydrocarbon radical, preferably a methyl group.

Preferably, in the formula (I'''), R$_4$ represents a hydroxyl group.

Specific compounds that can advantageously be implemented in the method according to the invention, and having a particularly high effectiveness in protection/repair of the skin, in particular by topical application onto the skin of an individual, satisfy the following formulas (Ia) to (Ih):

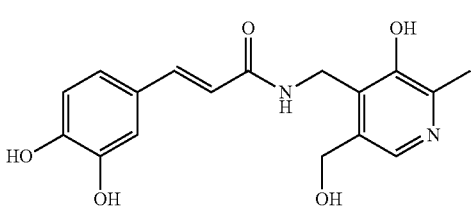

(Ia)

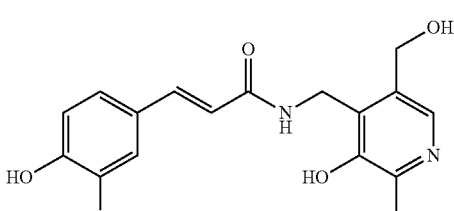

(Ib)

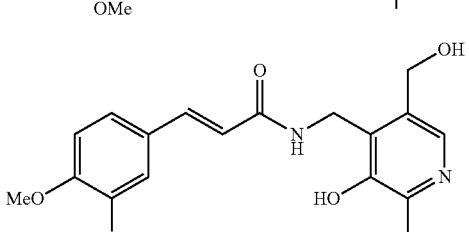

(Ic)

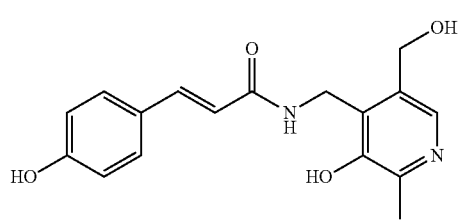

(Id)

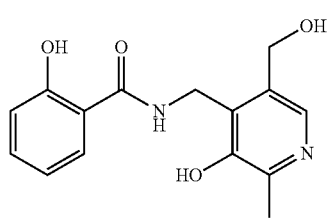

(Ie)

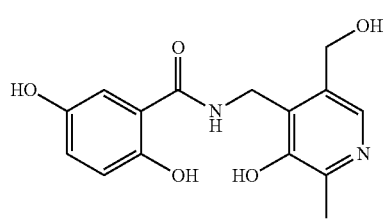

(If)

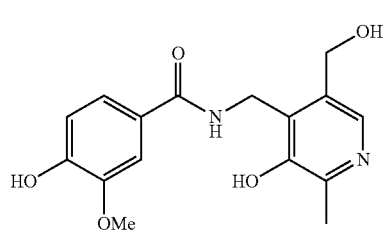

(Ig)

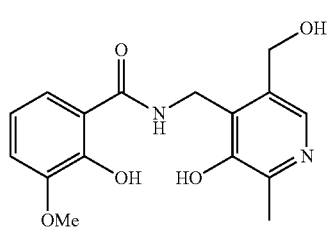

(Ih)

The compounds having the general formula (I) implemented in the method according to the invention can be synthesised by any method known to a person skilled in the art. They can in particular be synthesised by either a chemical pathway or by enzymatic catalysis, using for example a lipase such as the lipase B from *Candida antarctica* (CaL-B).

In specific modes of implementation of the invention, particularly advantageous in terms of effectiveness in prevention and repair of skin ageing, the compound according to the invention is present in the cosmetic composition at a concentration between 0.0000001 and 10% by weight with respect to the total weight of the composition, preferably at a concentration between 0.00001 and 2% by weight with respect to the total weight of the composition, and preferably between 0.001% and 2% by weight with respect to the total weight of the composition.

A plurality of compounds having the general formula (I) according to the invention can of course be used simultaneously, formulated in the same cosmetic composition.

The composition implemented in the method according to the invention can be in any form conventional per se, in particular, but not limitingly, in the form of a cream, ointment, milk, oil, unguent, lotion, powder, solution, gel, suspension, soap, soaked pad, or shampoo, etc., for topical use; or in the form of pills, capsules, granules, powders, etc., for oral administration.

It can further comprise any additive conventional per se in the field of cosmetics, such as a diluent, a preservative, stabiliser, emulsifier, adjuvant, carrier, etc.

The desired cosmetic effect can be reinforced by the implementation, in the composition, of any other additional active ingredient, having a beneficial effect for the skin, this effect possibly occurring or not occurring synergetically with that of the compound having the general formula (I) according to the invention. Such an additional active ingredient can in particular have an activity of reducing wrinkles, increasing the hydration of the skin, its firmness, reinforcing its barrier function, thickening the skin, etc. Examples of a active ingredients that can be implemented in association or in combination with a compound according to the invention include anti-ageing agents, anti-wrinkle agents, peeling agents, hydrating agents, depigmenting agents, propigmenting agents, anti-glycation agents, inhibitors of NO-synthase, agents stimulating the synthesis of dermal or epidermal macromolecules and/or preventing their degradation, agents stimulating the proliferation of fibroblasts and/or keratinocytes or stimulating the differentiation of the keratinocytes, myorelaxant agents, dermo-relaxing agents, tensing agents, anti-pollution and/or anti-radical agents, anti-irritant agents, agents acting on microcirculation, agents acting on the energy metabolism of the cells, anti-UV agents and their mixtures, such a list not being in any way limiting.

Such agents can be chosen from the carotenoids (for example beta-carotene, lycopene, astaxanthin, phytoenes), the retinoids (for example retinol, vitamin A, cis or trans retinoic acid, retinol esters), the flavanones, the flavonols, the isoflavones (for example genistein, daidzein, rutin, etc.), the coumarins, the lignans, the vitamins (for example A, B, C, E, F, K, H), the stilbenoids, the sapogenins, the pentacyclic triterpenic acids, the β-hydroxyacids, the hydroxyphenols and their ether, ester or heteroside derivatives, the phenolic acids, the monomers that are precursors of tannins, the amino sugars, the amino acids (for example arginine, lysin, tyrosine, cysteine, taurine, etc.), the peptides (for example carnosine, enkephalins, the commercial peptides proposed for their anti-ageing effect such as Pal-KTTKS (Matrixyl® from the company Sederma), Ac-Hexapeptide 3 (Argireline from the company Lipotec), Pal-GQPR (Rigin® from the company Sederma), Dermican, Ac-tetrapeptide 9 (Company BASF Beauty Solutions), Syn-ake, tripeptide (Company DMS/Pentapharm), and their mixtures, etc.

In particular, the composition according to the invention can contain, in addition to the compound having the general formula (I), one or more active principles chosen from: retinol, resveratrol, ascorbic acid, hyaluronic acid, tocopherol, nicotinamide, pantothenic acid, Aloe Vera (*Aloe Barbadensis*), Argan oil (*Argania Spinosa*), Shea butter (*Butyrospermum Parkii*), calendula (*Calendula Officinalis*), jojoba (*Buxus Chinensis*), squalane, glycerine, keratin and caffeine, such a list of course not being in any way limiting to the invention.

The method for cosmetic treatment of the skin according to the invention can in particular comprise the topical application, onto the skin surface of the relevant portions of the body of the individual needing it, for example onto the skin surface of the face, of a determined quantity of the composition containing the compound having the general formula (I) as an active principle, for example at a rate of one or two times per day, for example in the morning and in the evening, and for example for a period between 2 weeks and 2 months or more.

According to another aspect, the present invention relates to the use of a compound having the general formula (I) as defined above, or of one of the salts thereof, for the non-therapeutic, cosmetic treatment of the skin of an individual, in particular topically, in particular for the prevention and/or the repair of the signs of ageing of the skin, in particular with respect to exposure to external aggressions. This compound can, for this purpose, be comprised in a composition adapted to administration to humans, in particular by topical application onto the skin. This compound and this composition, as well as the modes of this use, can satisfy one or more of the features described above in reference to the cosmetic treatment method according to the invention.

More particularly, the invention relates to the use of a compound having the general formula (I) as defined above, or of one of the salts thereof, for, as a non-therapeutic cosmetic treatment of the skin:
- a detoxifying treatment,
- the treatment of oxidative stress,
- a treatment of the damage related to cigarette smoke,
- an anti-inflammatory and/or soothing treatment,
- and/or a treatment of the damage to the DNA caused by free radicals.

In the present description, treatment means both the prevention of damage to the skin, and the repair/care of the skin.

Another aspect of the invention relates to a cosmetic composition, intended in particular for the treatment of the skin, and in particular for the prevention and/or the repair of the effects of ageing of the skin, in particular related to external aggressions, and intended in particular for implementation in a method for cosmetic treatment of the skin according to the invention. This composition contains a compound having the general formula (I) as defined above, or one of the salts thereof, in a cosmetically acceptable vehicle.

This compound and this composition can satisfy one or more of the features described above in reference to the method for cosmetic treatment according to the invention.

The following compounds, however, are preferably excluded from this composition in the context of the present invention:
3-(2,4-dihydroxyphenyl)-N-(3-hydroxy-5-hydroxymethyl-2-methyl-pyridin-4-ylmethyl)-acrylamide
3-(3,5-dihydroxyphenyl)-N-(3-hydroxy-5-hydroxymethyl-2-methyl-pyridin-4-ylmethyl)-acrylamide
3-(2,6-dihydroxyphenyl)-N-(3-hydroxy-5-hydroxymethyl-2-methyl-pyridin-4-ylmethyl)-acrylamide The composition according to the invention can in particular contain one or more compounds satisfying the general formula (I″), preferably one or more compound satisfying the general formula (I″), and for example the compound having the formula (Ia) and/or the compound having the formula (Ic), these formulas being as defined above. In particular, the composition according to the invention can be in a form adapted to topical use.

It has been further observed by the present inventors that the compounds having the general formula (I), satisfying one or more of the above features, and in particular the compounds having the formula (I″), and in particular the compounds having the formula (I‴), have an anti-inflammatory effect, related to their action described above of inhibition of the expression of the cytokines secreted during one of the first cutaneous inflammatory responses, such as Interleukin 8 (IL8) and tumour necrosis factor (TNFα).

Thus, according to another aspect, the present invention relates to a compound having the general formula (I), or one of the salts thereof, for its therapeutic use for the treatment of an inflammatory disease of the skin, and in particular by topical administration onto a zone of the skin having said inflammatory disease. The compound having the general formula (I) can satisfy one or more of the features described above in reference to the method for cosmetic treatment according to the invention.

A method for therapeutic treatment of an inflammatory disease of the skin of an individual comprises the administration to said individual, in particular the topical application onto a zone of the skin of said individual affected by said inflammatory disease, of a compound having the general formula (I), or of one of the salts thereof. This compound having the general formula (I) can satisfy one or more of the features described above in reference to the method for cosmetic treatment according to the invention.

The invention also relates to a pharmaceutical/dermatological composition comprising such a compound, in a pharmaceutically acceptable vehicle. This composition, intended for humans and/or animals, can be advantageously adapted for topical administration onto the skin of an individual needing it.

This composition can satisfy one or more of the features described above in reference to the cosmetic composition according to the invention.

The features and advantages of the invention will be clearer in light of the examples of implementation below, provided simply for informational purposes and in no way limiting to the invention, with the support of FIGS. 1 to 7, in which:

BRIEF DESCRIPTION OF THE DRAWINGS

FIG. 5 shows fluorescence microscopy images obtained on an explant of skin after marking with haematoxylin and eosin, the explant being a/ non-irradiated untreated, b/ irradiated with UVAs untreated, c/ irradiated with UVAs treated with caffeic acid, d/ irradiated with UVAs treated with pyridoxamine, e/ irradiated with UVAs treated with the compound (Ia) according to the invention, f/ irradiated with UVAs treated with the compound (Ic) according to the invention, g/ irradiated with UVAs treated with the compound (Id) according to the invention, h/ irradiated with UVAs treated with the comparative compound Comp.1;

FIG. 6 shows fluorescence microscopy images obtained on an explant of skin after marking with γ-H2AX and with 4′,6-diamidino-2-phenylindole, the explant being a/ non-irradiated untreated, b/ irradiated with UVAs untreated, c/ irradiated with UVAs treated with caffeic acid, d/ irradiated with UVAs treated with pyridoxamine, e/ irradiated with UVAs treated with the compound (Ia) according to the invention, f/ irradiated with UVAs treated with the compound (Ic) according to the invention, g/ irradiated with UVAs treated with the compound (Id) according to the invention, h/ irradiated with UVAs treated with the comparative compound Comp.1;

EXAMPLE 1

Figure 1:
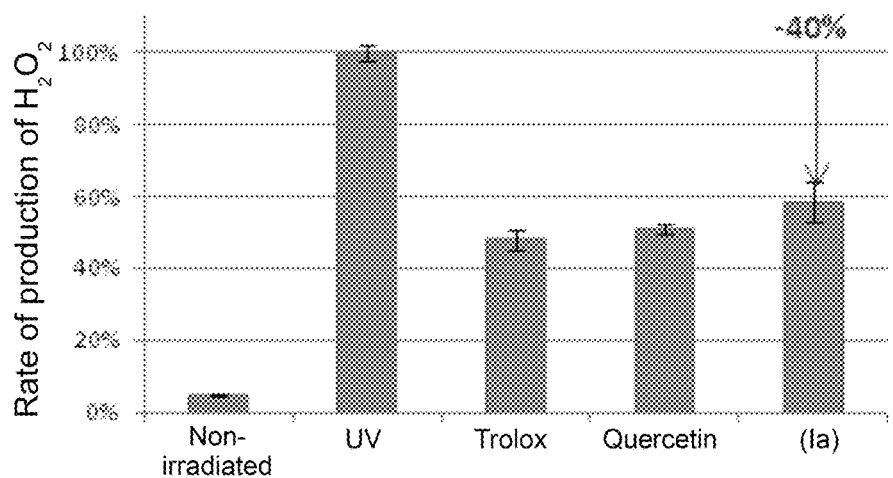
FIG. 1 shows a bar graph showing the rate of production of $H_2O_2$ by normal human keratinocytes subjected to stress with UVA rays, without treatment (UV), or with a treatment by Trolox, Quercetin, or by the compound (Ia) according to the invention, or for non-irradiated cells.

Chemical Synthesis of Compounds According to Specific Modes of Implementation of the Invention General Synthesis Protocol For this Example, the synthesis protocol is the following.

In a round-bottom flask inside which a magnetised bar has been placed, Ag of component A, Dg of component D and then Cg divided by 2 of component C are successively weighed. The round-bottom flask is placed under an inert atmosphere.

Then, FmL of 1,3-dioxolane are added into the round-bottom flask. The round-bottom flask is then magnetically stirred in an oil bath at 60° C. for 30 min.

Bg of component B, Cg divided by 2 of component C then GmL of triethylamine (Et₃N) are then added.

The mixture is then placed in reflux in a bath at 60° C.

The reaction is monitored on Thin-Layer Chromatography (TLC) (eluent: 7AE/1MeOH/2chloroform, visualisation at 254 nm, Rf=0.28).

After 3 h of reaction, the solution is left to return to ambient temperature.

100 mL of ethyl acetate (EA) are then added into the crude reaction mixture. An operation of washing with 20 mL of aqueous solution and then two successive operations of extraction with 100 mL of ethyl acetate (EA) are carried out. The organic phase is recovered and concentrated at a reduced pressure.

Purification by "flash" chromatography on a column of 20-40 μm silica is carried out, with the eluents: Eluent n°1: EA; Eluent n°2: (1MeOH/1,5chloroform).

The fractions of interest are recovered, combined and concentrated at a reduced pressure.

Compound (Ia)

The compound according to the invention (E)-N-((3-hydroxy-5-(hydroxymethyl)-2-methylpyridin-4-yl)methyl)-3-(3,4-dihydroxyphenyl)acrylamide, having the formula (Ia):

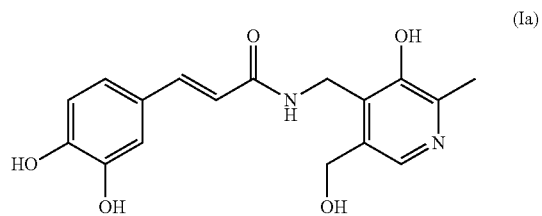

wherein $R_1$, $R_2$, $R_5$ each represent a hydrogen atom, $R_3$ and $R_4$ each represent a hydroxyl group, $R_6$ and $R_8$ each represent a hydroxyl group, $R_7$ represents a methyl group, and Z represents a group having the formula (II) in which Y represents an ethylenyl radical, is prepared as indicated in the general protocol above, with the components in the following quantities:

Component A: caffeic acid/A=1 g

Component B: pyridoxamine dihydrochloride (97%)/B=2 g

Component C: 1-ethyl-3-(3-dimethylaminopropyl)carbodiimide (EDC.HCl) (98%)/C=1.6 g Component D: hydroxybenzotriazole (HOBt) (98%)/D=0.9 g 1,3-dioxolane: Volume F=30 ml Et₃N: Volume G=2.81 ml Finally, 917 mg of a light yellow solid are recovered (M=330.34 g·mol⁻¹; tr(LCMS)=3.72 min, ρ=50%; LC purity>98%).

The chromatographic analysis method (LCMS) is the following: Gemini NX C18 50×4.6 mm 5 μm Column; eluents: water+0.1% formic acid (HCOOH)/acetonitrile+0.1% HCOOH; flow rate 1 ml/min, beginning of the gradient: 95-5, isocratic gradient for 1 minute: 95-5, after 4 min: 0-100, then isocratic gradient for 2 minutes: 0-100, and return to 95-5 in 1 min. Detection by a UV detector.

Proton NMR analysis (¹H; δ in ppm) CD₃OD: 8.10 (1H), 7.51 (2H, dd, J=15 Hz, J=6 Hz), 7.02 (2H, dd, J=6.3 Hz, J=1.8 Hz), 6.94 (1H, dd, J=4.2 Hz, J=2.1 Hz), 6.90 (1H, dd, J=4.2 Hz, J=2.1 Hz), 6.76 (2H, dd, J=8.1, J=2.7), 6.39 (1H, d, J=15.6 Hz), 6.21 (1H, d, J=15.6 Hz), 4.60 (2H), 2.60 (3H).

Compound (Ib)

The compound according to the invention (E)-3-(4-hydroxy-3-methoxyphenyl)-N-((3-hydroxy-5-(hydroxymethyl)-2-methylpyridin-4-yl)-methyl)-acrylamide, having the formula (Ib):

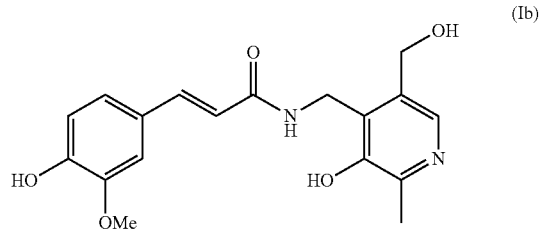

wherein $R_1$, $R_2$, $R_5$ each represent a hydrogen atom, $R_3$ represents a hydroxyl group, $R_4$ represents an —OR′ group in which R' represents a methyl group, $R_6$ and $R_8$ each represent a hydroxyl group, $R_7$ represents a methyl group, and Z represents a group having the formula (II) in which Y represents an ethylenyl radical, is prepared as indicated in the general protocol above, with the components in the following quantities:
Component A: ferulic acid/1 g
Component B: pyridoxamine dihydrochloride (97%)/1.9 g
Component C: 1-ethyl-3-(3-dimethylaminopropyl)carbodiimide (EDC.HCl) (98%)/1.6 g
Component D: hydroxybenzotriazole (HOBt) (98%)/0.9 g
1,3-dioxolane: Volume E=30 ml
$Et_3N$: Volume F=2.81 ml Finally, 958 mg of a yellow solid are recovered (M=344.37 g·mol$^{-1}$; tr(LCMS)=5.78 min, ρ=54%; LC purity>90%).

The chromatographic analysis method (LCMS) is the following: Gemini NX C18 150×4.6 mm 5 μm Column; eluents: water+0.1% formic acid (HCOOH)/acetonitrile+ 0.1% HCOOH; flow rate 1 ml/min, beginning of the gradient: 95-5, after 9 min: 5-95, then isocratic gradient for 1 min: 5-95, and return to 95-5 in 1 min. Detection by a UV detector.

The chromatographic analysis method (LCMS) is as indicated above for the compound (Ia), but with: beginning of the gradient: 95-5, isocratic gradient for 1 minute: 95-5, after 4 min: 0-100, then isocratic gradient for 2 minutes: 0-100, and return to 95-5 in 1 min.

Compound (Ic)

The compound according to the invention (E)-3-(3-hydroxy-4-methoxyphenyl)-N-((3-hydroxy-5-(hydroxymethyl)-2-methylpyridin-4-yl)-methyl)-acrylamide, having the formula (Ic):

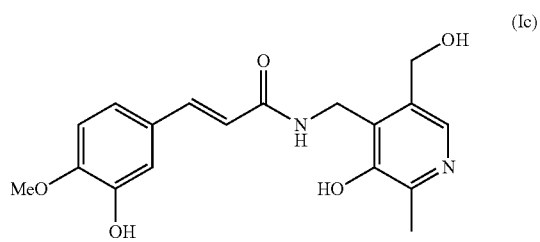

(Ic)

wherein $R_1$, $R_2$, $R_5$ each represent a hydrogen atom, $R_4$ represents a hydroxyl group, $R_3$ represents an —OR' group in which R' represents a methyl group, $R_6$ et $R_5$ each represent a hydroxyl group, $R_7$ represents a methyl group, and Z represents a group having the formula (II) in which Y represents an ethylenyl radical, is prepared as indicated in the general protocol above, with the components in the following quantities:
Component A: isoferulic acid/1 g
Component B: pyridoxamine dihydrochloride (97%)/1.9 g
Component C: 1-ethyl-3-(3-dimethylaminopropyl)carbodiimide (EDC.HCl) (98%)/1.6 g
Component D: hydroxybenzotriazole (HOBt) (98%)/0.9 g
1,3-dioxolane: Volume E=30 ml
$Et_3N$: Volume F=2.81 ml Finally, 1028 mg of a light beige solid are recovered (M=344.37 g·mol$^{-1}$; tr(LCMS)=5.82 min, ρ=58%; LC purity>99%).

The chromatographic analysis method (LCMS) is as indicated above for the compound (Ia), but with: beginning of the gradient: 95-5, after 9 min: 5-95, then isocratic gradient for 1 min: 5-95, and return to 95-5 in 1 min.

Compound (Id)

The compound according to the invention (E)-N-((3-hydroxy-5-(hydroxymethyl)-2-methylpyridin-4-yl)-methyl)-3-(4-hydroxyphenyl)-acrylamide, having the formula (Id):

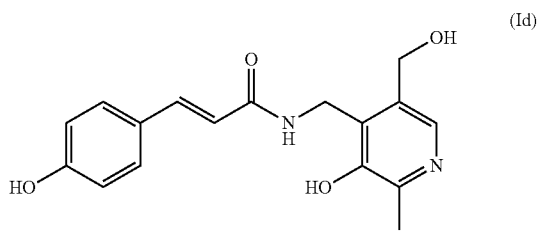

wherein $R_1$, $R_2$, $R_4$, $R_5$ each represent a hydrogen atom, $R_3$ represents a hydroxyl group, $R_6$ and $R_5$ each represent a hydroxyl group, $R_7$ represents a methyl group, and Z represents a group having the formula (II) in which Y represents an ethylenyl radical, is prepared as indicated in the general protocol above, with the components in the following quantities:
Component A: coumaric acid/1 g
Component B: pyridoxamine dihydrochloride (97%)/2.2 g
Component C: 1-ethyl-3-(3-dimethylaminopropyl)carbodiimide (EDC.HCl) (98%)/1.6 g
Component D: hydroxybenzotriazole (HOBt) (98%)/0.9 g
1,3-dioxolane: Volume E=30 ml
$Et_3N$: Volume F=2.81 ml Finally, 824 mg of a light beige solid are recovered (M=314.34 g·mol$^{-1}$; tr(LCMS)=5.70 min, p=43%; LC purity>99%).

The chromatographic analysis method (LCMS) is as indicated above for the compound (Ia), with: beginning of the gradient: 95-5, after 9 min: 5-95, then isocratic gradient for 1 min: 5-95, and return to 95-5 in 1 min.

The compounds (Ie) to (Ih) are synthesised according to the same operating mode as the compounds (Ia) to (Id).

EXAMPLE 2

Synthesis by Enzymatic Catalysis of the Compound (Ia) According to a Specific Embodiment of the Invention The reaction is initiated by the addition of 360 mg of Novozym 435 lipase into 100 mL of terbutanol containing 40 mM of caffeic acid, 100 mM of dichrorohydrated pyridoxamine, and 360 mg of activated molecular sieve. The suspension is stirred at 200 rpm for 3 days at 37° C.

The reaction is followed by Thin-Layer Chromatography (TLC) (eluent: 7AE/1MeOH/2chloroform, visualisation at 254 nm, Rf=0.28).

The suspension is then filtered on sintered material and the filtrate is concentrated at a reduced pressure.

Purification by "flash" chromatography on a column of 20-40 μm silica, with the eluents: Eluent n°1: EA; Eluent n°2: (1MeOH/5chloroform).

The fractions of interest are recovered, combined, and concentrated at a reduced pressure.

Finally, 462 mg of a light yellow solid are recovered (M=330.34 g·mol$^{-1}$; tr(LCMS)=3.72 min, ρ=35%; LC purity>98%).

The chromatographic analysis method (LCMS) is similar to that described above in Example 1 in reference to the compound (Ia).

Proton NMR analysis ($^1$H; δ in ppm) CD$_3$OD: 8.10 (1H), 7.51 (2H, dd, J=15 Hz, J=6 Hz), 7.02 (2H, dd, J=6.3 Hz, J=1.8 Hz), 6.94 (1H, dd, J=4.2 Hz, J=2.1 Hz), 6.90 (1H, dd, J=4.2 Hz, J=2.1 Hz), 6.76 (2H, dd, J=8.1, J=2.7), 6.39 (1H, d, J=15.6 Hz), 6.21 (1H, d, J=15.6 Hz), 4.60 (2H), 2.60 (3H).

EXAMPLE 3

Effect of the Compound (Ia) According to the Invention on the Expression of Proteins Involved in Inflammation This study is carried out on normal human Keratinocytes (NHEK).

In this example, the anti-inflammatory properties of the compound (Ia) are evaluated by the assay of the IL-8, after the application of the cytokine IL-1β at 10 ng/ml onto NHEKs. IL-8 is a major inflammatory cytokine produced first of all during the inflammatory response of the keratinocytes. The quantification of the IL-8 in the culture supernatants allows an evaluation of the inflammatory state of the cells.

The IL-1β is added to the culture medium of the NHEKs at a rate of 10 ng/ml for 24 h. After incubation, the culture media are removed and replaced with culture media containing the compound (Ia) at 3 ppm. After 24 h of incubation, the supernatants are collected.

The reference anti-inflammatory element is dexamethasone (Sigma) used at 0.4 ppm. A control having undergone the same experimental conditions without the compound (Ia) (CTL), as well as a non-induced control (CTL without IL-1β), are also carried out.

The quantification of the IL-8 in 50 μl of the culture supernatants is measured by an ELISA test (human CXCL8/IL-8 Immunoassay, R&D Systems).

Each treatment is carried out in triplicate.

The results obtained are shown in table 1.

TABLE 1

Effect of the compound (Ia) on the expression of proteins involved in the inflammation of normal human keratinocytes (NHEK)

| Supernatants tested | Quantification of the IL8 (optical density) |
|---|---|
| CTL without IL-1β | 0.06 |
| CTL | 0.23 |
| IL-1β + Dexamethasone 0.4 ppm | 0.13 |
| IL-1β + compound (Ia) 3 ppm | 0.16 |

The analysis of the results obtained shows that the compound (Ia) according to the invention reduces, in a very highly significant manner (p<0.001), the quantity of IL-8 produced by the keratinocytes after the induction of the inflammatory state by IL-1β, with respect to the control keratinocytes CTL. The compound (Ia) thus inhibits, by 30%, the production of IL8 in the keratinocytes subjected to the inflammation in the presence of IL-1β.

EXAMPLE 4

Effect of the Compound (Ia) According to the Invention on the Production of Reactive Oxygen Species (ROS) after UV-Induced Oxidative Stress The cells used for this example are normal human Keratinocytes (NHEK).

The antioxidant properties (neutralising the production of reactive oxygen species) of the compound (Ia) are evaluated after a single stress with UVAs on NHEKs, by a test based on the use of the fluorescent probe H2DCFDA on a triple culture.

H2DCFDA (2'-7'dichlorodihydrofluorescein diacetate, Fischer Scientific) is a probe that, after having diffused into the cell and after its acetate group has been split by intracellular esterases, can be oxidised by free radicals (H$_2$O$_2$) into DCF (2'-7' dichlorofluorescein), a fluorescent compound. The production of the free radicals can thus be quantified by the level of fluorescence emitted by the oxidised probe. The more the cell produces free radicals, the higher the level of fluorescence detected.

After 24 hours of incubation with the compound (Ia) (3 ppm in an aqueous solution with 0.1% dimethylsulfoxide) or the reference elements, the cells are placed in the presence of the H2DCFDA probe at 3 ppm for 1 hour at 37° C., 5% CO$_2$ in order to allow its intracellular diffusion.

The reference antioxidant elements are: Trolox (6-hydroxy-2,5,7,8-tetramethylchroman, Sigma), at 20 ppm and Quercetin (quercetin dihydrate, Sigma), at 18 ppm.

After one rinsing, the cells are subjected to a single stress with UVAs (in the absence of compound (Ia)) at a rate of 10 joules per square centimetre. The quantification of the fluorescence emitted (excitation: 485 nm; emission: 520 nm) is carried out immediately after the end of the UVA stress.

The control (CTL UVA) corresponds to the cells having undergone the same treatment as cells incubated with the compound (Ia), but without this compound. A control not exposed to the UVAs is also carried out (CTL without stress).

In order to provide a result representative of the cellular population of each condition after a single stress with UVAs, a cellular viability test (MTS) is carried out immediately after the quantification of the fluorescence emitted. The fluorescence values are thus normalised with respect to the cellular viabilities in order for it to be possible to compare the levels of fluorescence of the various conditions to each other. The results obtained are presented in table 2 below.

TABLE 2

Assay of the fluorescence with DCFDA after irradiation of with UVAs, for NHEKs cells treated or not treated with the compound (Ia) according to the invention

| Supernatants/compounds tested | Assay of the fluorescence with H2DCFDA after irradiation of NHEKs with UVAs |
|---|---|
| CTL without stress | 16441.9 |
| CTL UVA | 289687.6 |
| UV + Trolox 20 ppm | 269830.3 |
| UV + Quercetin 18 ppm | 207589.6 |
| UV + compound (Ia) 3 ppm | 198588.8 |

FIG. 1 illustrates, in the form of a bar graph, the rate of production of H$_2$O$_2$ for each condition tested.

The analysis of the results obtained shows that the compound (Ia) reduces, in a very highly significant manner (p<0.001), the level of intracellular H$_2$O$_2$ produced after a single stress with UVAs. At the low concentration tested, as can be clearly seen in FIG. 1, the compound (Ia) reduces, by 40%, the generation of intracellular H$_2$O$_2$ in the cells in response to this stress.

The compound (Ia) according to the invention preserves the integrity of the skin cells and limits the ageing induced by the overexpression of free radicals, which demonstrates its antioxidant activities.

EXAMPLE 5

Protecting Effect of the Compound (Ia) According to the Invention in Presence of Polluting Stress The cells used for this example are normal human Fibroblasts (NHDF).

A cellular viability test with cadmium is carried out in order to know the protective effect of the compound (Ia) against polluting stress. Cadmium (Cd) is a toxic and ecotoxic heavy metal found in the environment.

The cells are cultured at the concentration of 7000 cells per well of 96-well plates.

The pretreatment is carried out 24 hours after the inoculation of the cells with the compound (Ia) at 10 ppm in an aqueous solution with 0.1% dimethylsulfoxide, or without compound (Ia) for 24 hours.

After the pretreatment, a treatment with cadmium is carried out. The cells are placed in the presence of cadmium at 3 ppm+compound (Ia) at 10 ppm, or only in the presence of cadmium at 3 ppm (CTL) for 24 hours at 37° C., 5% $CO_2$. The control without stress (CTL without stress) corresponds to the cells not having undergone a treatment with cadmium.

The plates are read with a Multiskan® at 450 nm and the results obtained are presented in table 3 below.

TABLE 3

Cellular viability, after exposure or non-exposure to cadmium, of normal human fibroblasts, treated or not treated with the compound (Ia) according to the invention

| Compounds tested | Cellular viability during the exposure or non-exposure to cadmium (optical density) |
|---|---|
| CTL without stress | −1.30 |
| CTL (Cd 3 ppm) | 0.95 |
| Cd 3 ppm + compound (Ia) 10 ppm | 1.28 |

The analysis of the results obtained shows that the compound (Ia) according to the invention maintains the cellular viability after exposure to cadmium, which demonstrates its protective effect in presence of polluting stress by heavy metals.

EXAMPLES 6 to 9

Study of the Properties of the Compound (Ia) According to the Invention for Fighting the External Stresses Induced by UVs In these examples, the protective properties of the compound (Ia) against the damage caused to the DNA and to the extracellular matrix by repeated UVA irradiation, are measured on explants of human skin (NATIVESKIN, Genoskin).

Upon reception of the explants, the latter are topically coated with Carbopol® (Lubrizol)+DMSO for the non-UVA control (CTL without stress) and for the control with stress by UVAs (CTL UVA), and with Carbopol®+compound (Ia) at 100 ppm for the test.

Over three days, the cells are subjected to three stresses with UVAs at a rate of 50 joules per square centimetre.

The first irradiation takes place 24 hours after the treatments. The products are present before, during and after the irradiation. The control without stress is wrapped in aluminium and also placed in the irradiator.

During the irradiation, the explants inserted are disposed in a petri dish with PBS. Fresh medium (Genoskin Culture medium) is added after the irradiation.

After the third day of irradiation, the explants are cultivated for 24 hours, then collected and fixed for 48 hours in formalin (Sigma). The samples are included in paraffin and cut.

EXAMPLE 6

Protection Against the Damage to the DNA Caused by Repeated UVA Irradiation by the Compound (Ia) According to the Invention γ-H2Ax marking by immunofluorescence on a paraffin section is carried out, in order to detect the double-strand breaks of the DNA.

The samples are prepared for the fluorescent marking. After deparaffining, the samples are unmasked by a citrate bath. After rinsing and blocking, the samples are incubated in the presence of the primary antibody, γ-H2Ax (Cell Signaling Technology), then incubated in the presence of the secondary antibody (Invitrogen) bonded to fluorescein for 1 hour. After washing, the samples are then placed in the presence of DAPI for 10 min in order to mark the nuclei, then rinsed once again.

Figure 2:
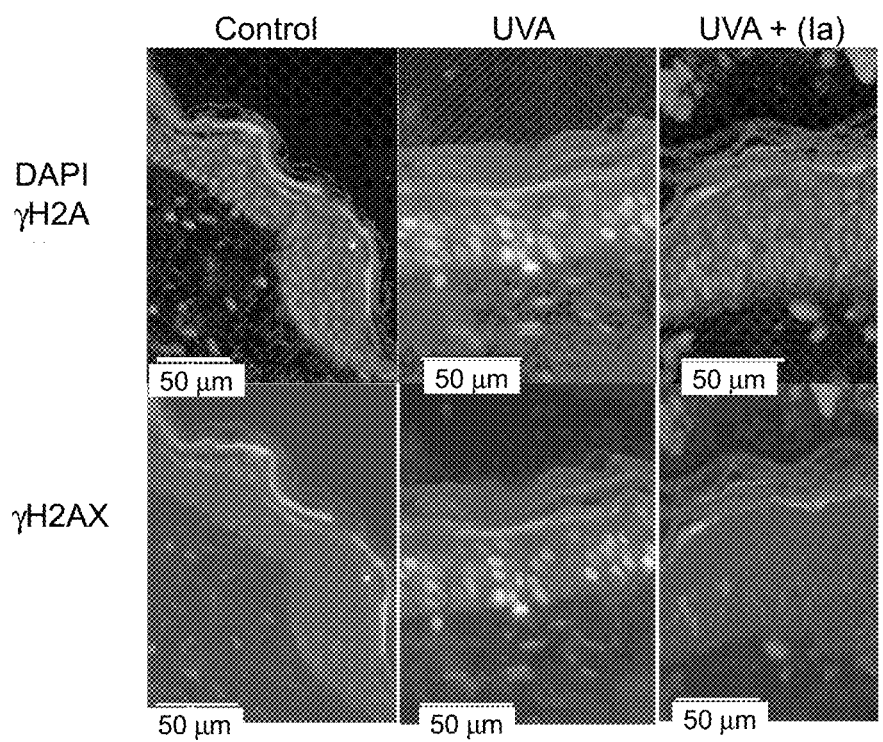
FIG. 2 shows sections, observed with a microscope, of explants of skin having been subjected to stress with UVAs, treated (UVA+(Ia)) or not (UVA) by a compound (Ia) according to the invention, after γ-H2Ax marking by immunofluorescence or colouring with DAPI—the control corresponding to cells not subjected to UVA rays.

The sections are mounted on a slide, and observed using a microscope (Leica DM5000B). The images obtained are shown in FIG. 2. An absence of fluorescence is clearly observed for the sample treated with the compound (Ia) according to the invention, which corresponds to an absence of double-strand breaks of the DNA.

The fluorescence is quantified by means of the microscope. The results obtained are presented in table 4 below.

TABLE 4

Analysis of the effect of the compound (Ia) on the reduction of double-strand breaks of the DNA induced by the UVAs

| Compounds tested | Cells positive for γ-H2Ax marking based on 100%/ to the total number of cells |
|---|---|
| CTL without stress | 4.34%-47/1116 |
| CTL UVA | 33.93%-381/1123 |
| Compound (Ia) 100 ppm | 4.76%-59/1282 |

The analysis of the results obtained shows a very highly significant reduction in the number of cells positive for γ-H2Ax marking in the presence of the compound (Ia), with respect to the irradiated explant ($p<0.001$, Welch's t-test).

This study demonstrates the effectiveness of the compound (Ia) according to the invention in the protection against the damage to the DNA caused by repeated UVA irradiation, the number of cells positive for the γ-H2Ax marking being then extremely small, substantially equal to that of the non-irradiated cells.

EXAMPLE 7

Effect of Protection and In-Depth Regeneration of the Skin by the Compound (Ia) According to the Invention A morphological study of the skin is implemented.

The samples of explant are deparaffined, rehydrated and then they are subjected to colouration with haematoxylin and with eosin in order to observe the in-depth effect of the compound (Ia) on the skin. The slides are then dehydrated.

Figure 3:
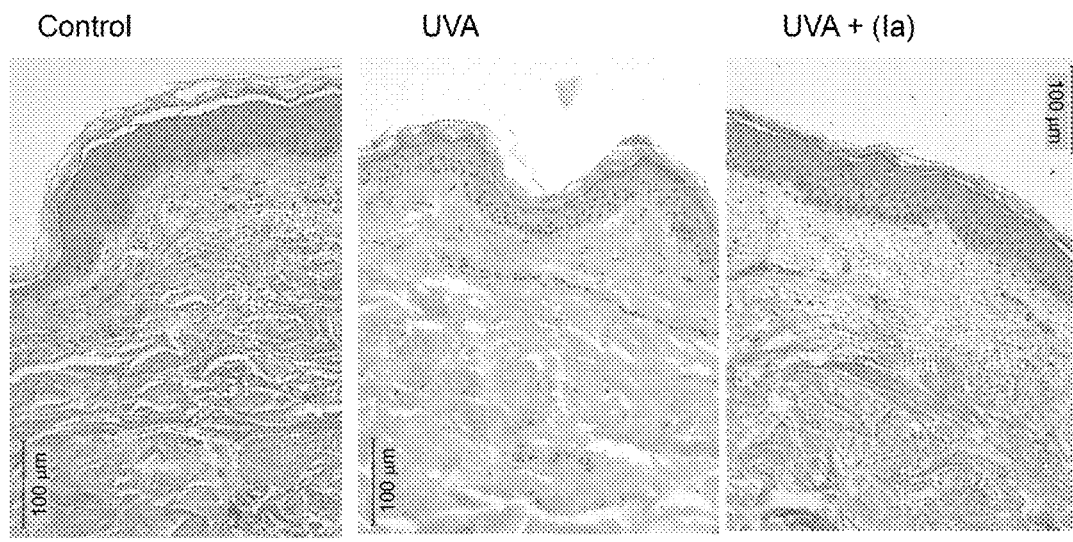
FIG. 3 shows images taken with a microscope (magnification 20×) of explants of skin having been subjected to stress with UVAs, treated (UVA+(Ia)) or not (UVA) by a compound (Ia) according to the invention, after colouring with haematoxylin—the control corresponding to cells not subjected to UVA rays.

The Leica DM5000B microscope with a magnification of X20 is used to carry out the observations in 2D. The results are shown in FIG. 3.

In it, it is observed that the UVA treatment induces a reduction in the thickness of the epidermis, a disorganisation of the epidermal layers and an accumulation of corneocytes.

The compound (Ia) according to the invention protects and repairs: the epidermal barrier is preserved from the degradation by the UVAs and the structure of the dermis is preserved.

EXAMPLE 8

Effect of the Compound (Ia) According to the Invention on the Expression of the Protein MMP1 (Matrix-Metalloprotease of Type 1)

A marking of the protein MMP1 by immunofluorescence on a paraffin section is carried out.

The samples are prepared for the fluorescent marking. After deparaffining, the samples are unmasked by a citrate bath. After rinsing and blocking, the samples are incubated in the presence of the primary antibody MMP1 (Abcam) then incubated in the presence of the secondary antibody (Invitrogen) for 1 hour. After washing, the samples are then placed in the presence of DAPI for 10 min in order to mark the nuclei, then rinsed once again.

The sections are mounted on a slide and the fluorescence is quantified using a microscope (Leica DM5000B). The results obtained are presented in table 5 below.

TABLE 5

Expression of MMP1 in the cells treated or not treated by the compound (Ia) according to the invention

| Compounds tested | Cells positive for MMP1 based on 100% - Average fluorescence intensity of the MMP1 marking (AU) |
| --- | --- |
| CTL without stress | −141.6 |
| CTL UVA | +16.7%-165.2 |
| Compound (Ia) 100 ppm | +3.2%-146.2 |

An increase in the marking in the dermis is observed with the UVA irradiation ($p<0.001$). After the treatment with the compound (Ia), the expression of the protein is similar to that obtained for the control without stress, and this in a significant manner ($p<0.05$).

This study demonstrates the effectiveness of the compound (Ia) according to the invention in the protection against the damage to the extracellular matrix caused by repeated UVA irradiation with the preservation of the expression of the protein MMP-1.

EXAMPLE 9

Effect of the Compound (Ia) According to the Invention on the Expression of the Protein ELN (Elastin)

Marking of the protein elastin is carried out by immunofluorescence on a paraffin section.

The samples are prepared for the fluorescent marking. After deparaffining, the samples are unmasked by a citrate bath. After rinsing and blocking, the samples are incubated in the presence of the primary antibody ELN (Abcam) then incubated in the presence of the secondary antibody (Invitrogen) for 1 hour. After washing, the samples are then placed in the presence of DAPI for 10 min in order to mark the nuclei, then rinsed once again.

The sections are mounted on a slide and the fluorescence is quantified using a microscope (Leica DM5000B). The results obtained are presented in table 6 below.

TABLE 6

Expression of the elastin in the cells treated or not treated by the compound (Ia) according to the invention

| Compounds tested | Cells positive for ELN based on 100% - Average fluorescence intensity of the marking ELN (AU) |
| --- | --- |
| CTL without stress | −160.4 |
| CTL UVA | −9%-145.9 |
| Compound (Ia) 100 ppm | +14%-182.4 |

This study demonstrates the effectiveness of the compound (Ia) according to the invention in the protection against the damage to the extracellular matrix caused by repeated UVA irradiation, with the preservation of the expression of the protein elastin. An effect of preservation of the skin from the phenomenon of senescence is also obtained.

EXAMPLE 10

Effect of the Compound (Ia) According to the Invention on the Protein Expression of Sirtuin-6

The cells used for this example are normal human Fibroblasts (NHDF).

In this example, the expression of Sirtuin-6 is measured at the protein level by the technique of immunofluorescence, after in vitro incubation of the cells in the absence or in the presence of compound (Ia) at a concentration of 10 ppm in an aqueous solution with 0.1% dimethylsulfoxide (DMSO).

The cells are cultured at the concentration of 5000 cells per well of 96-well plates, in the presence of standard culture medium for NHDF.

The contact with the compound (Ia) is carried out for 24 hours.

TGFβ is used as a positive control at the concentration of 10 ng/ml in an aqueous solution. A non-treated control is also carried out.

The supernatant is eliminated and the cells are prepared for the fluorescent marking. The cells are fixed in the presence of 3.7% formaldehyde, then permeabilised in a buffer containing 1% Triton®, finally the cells are rinsed and incubated in the presence of an anti-SIRT6 antibody (Abcam) for 2 hours. After washing, the cells are incubated in the presence of the secondary antibody (Alexa GAR488, Invitrogen) for 1 h. After washing, the cells are incubated in the presence of DAPI for 10 min, then rinsed once again.

The fluorescence is then quantified using an automated microscope (ArrayScan® (Cellomics®)).

The result obtained, in terms of expression of the Sirtuin-6 with respect to the basal level, is presented in table 7 below.

TABLE 7

Effects of the compound (Ia) on the protein expression of Sirtuin-6 in NHDF cells

| Compounds tested | Protein expression of the Sirtuin-6 compared to the basal level, based on 100% |
|---|---|
| Basal | 100% |
| Compound (Ia) 10 ppm | 113.69% |

It is observed that the compound (Ia) according to the invention stimulates the protein expression of Sirtuin-6 in a very highly significant manner ($p<0.001$). The expression of the Sirtuin-6 is very strong in the nucleus of the cells, a sign that the fluorescence is high and that the marking is very strong. Such an increase thus represents a considerable activation of the expression of the protein. Since the Sirtuin-6 is located in the nucleus of the cell and associated with chromatin, participating in the general preservation of the stability of the genome, and being involved in the repair of double-strand breaks of the DNA, in the repair via base excision and in the protection of the telomers, these results demonstrate that the compound (Ia) according to the invention promotes the repair of DNA.

Moreover, it has been demonstrated by the present inventors that the compound (Ia) according to the invention stimulates the expression of the gene of the Sirtuin-6 by 66% with respect to the untreated control (see Example 13 below).

EXAMPLES 11 and 12

Study of the Effect of the Compound (Ia) According to the Invention on the Expression of Genes of Skin Cells In these examples, the expression of the messenger RNA is measured by the technique of quantitative RT-PCR (reverse transcription followed by polymerase chain reaction), after incubation in vitro of the various cell types in the absence or in the presence of compound (Ia).

This study was carried out on normal human dermal Fibroblasts (NHDF) or normal human epidermal Keratinocytes (NHEK). The compound (Ia) is tested at $10^{-5}$M in an aqueous solution with 0.1% dimethylsulfoxide.

The cells are cultured at the concentration of 10,000 cells per well of 96-well plates, in the presence of standard culture medium according to the cell type.

The compound (Ia) is then added at the concentration (3 ppm), for 24 hours.

The supernatant is eliminated and the cells are taken up in a specific buffer for the extraction of the messenger RNA (mRNA). The mRNA is purified and reverse transcribed in the presence of a commercial reverse transcriptase.

The complementary DNA (cDNA) obtained is quantified by RT-PCR, by means of suitable primers. The rate of expression of the mRNA is normalised with 5 reference genes.

EXAMPLE 11

Effect of the Compound (Ia) According to the Invention on the Expression of Genes Coding for the Proteins of the Extracellular Matrix (Matrix-Metalloprotease of Type 3 and Type 9)

The cells used for this example are normal human keratinocytes (NHEK).

The results obtained, in terms of reduction of the expression of MMP-3 and MMP-9 with respect to the basal level (absence of compound), are shown in table 8 below.

TABLE 8

Effect of the compound (Ia) on the expression of MMP-3 and MMP-9 by NHEK cells treated or not treated by the compound (Ia)

| Genes tested | Reduction of the gene expression compared to the basal level based on 100% |
|---|---|
| MMP-3 | −50% |
| MMP-9 | −75% |

These results show that the compound (Ia) strongly protects the proteins of the extracellular matrix of the skin, and allows a reduction in the level of expression of the proteins MMP-3 and MMP-9 by the keratinocytes. Such a reduction induces a slowing down of the degradation of numerous components of the extracellular matrix (Fibronectin, Laminin, Collagens and Proteoglycans).

EXAMPLE 12

Effect of the Compound (Ia) According to the Invention on the Gene Expression of TNFα (Tumour Necrosis Factor) and IL8 (Interleukin 8)

The cells used for this example are normal human keratinocytes (NHEK).

The results obtained, in terms of reduction of the expression of TNFα and IL8 with respect to the basal level (absence of compound), are shown in table 9 below.

TABLE 9

Effect of the compound (Ia) on the TNFα and IL8 expression by NHEK cells treated or not treated by the compound (Ia)

| Genes tested | Reduction of the gene expression compared to the basal level based on 100% |
|---|---|
| TNFα | −45% |
| IL8 | −75% |

This shows that at the low concentration tested, the compound (Ia) reduces the expression of the genes TNFα and IL8 in a significant manner, which promotes the soothing of the skin.

EXAMPLE 13

Effect of the Compound (Ia) According to the Invention on the Gene Expression of Sirtuin-6

Located in the nucleus of the cell and associated with chromatin, Sirtuin-6 participates in the general preservation of the stability of the genome. It is involved in the repair of double-strand breaks, in the repair by base excision, and in the protection of the telomers.

The cells used for this example are normal human Fibroblasts (NHDF) The cells are inoculated in 96-well plates at a concentration of 10000 cells per well.

The contact with the compound tested is carried out for 24 h. After the 24 h contact, the supernatant is eliminated and the cells are collected in a lysis solution in order to extract the mRNA. The mRNA is reverse transcribed into DNA then quantified by real-time quantitative PCR.

The results obtained, in terms of expression of the Sirtuin-6 compared to the basal level (absence of compound) based on 100%, are shown in table 10 below.

TABLE 10

Effect of the compound (Ia) on the gene expression of the Sirtuin-6 in NHDF cells

| Compounds tested | Gene expression of the sirtuin-6 compared to the basal level based on 100% |
|---|---|
| Basal | 100% |
| Compound (Ia) | 166% |

A significant increase in the level of expression of the Sirtuin-6 is observed after contact with the compound (Ia) according to the invention, which means that the compound stimulates the gene of the Sirtuin-6, and promotes the repair of DNA.

EXAMPLE 14

Protective and/or Repair Effect of the Compound (Ia) According to the Invention after the Damage Induced by a Cigarette Extract The cells used for this example are normal human Fibroblasts (NHDF) and normal human epidermal Keratinocytes (NHEK).

A cigarette extract is prepared using a laboratory device allowing the sucking up of cigarette smoke via a suction system, and the controlled bubbling of this cigarette smoke into the solution studied, which is then filtered on a 0.22 μm filter made of Polyether sulfone (PES).

The cells are cultured at the concentration of 7000 cells per well of 96-well plates (NHDF) or 8000 cells per well (NHEK), in the presence of standard culture medium for NHDF or NHEK (for 24 h 37° C., 5% $CO_2$).

After pretreatment of the cells with the compound (Ia) at 10 ppm for 24 h the cells are treated with the cigarette extract diluted to $1/50^{th}$ in the culture medium with or without the compound (Ia) at 10 ppm for 24 h. The absorbance is read a first time at 450 nM (Multiskan®).

Then, 10 μl of WST1 (Roche) are introduced into the medium and the cells are incubated for 3 hours.

The absorbance at 450 nm is measured after the addition of WST1 (Multiskan®) and the results obtained, in terms of cellular viability, are shown in tables 11 and 12 below. The treated cells (Cigarette extract+(Ia)) are compared to the untreated cells (Control) or to the cells having only undergone exposure to the cigarette extract (Cigarette extract).

TABLE 11

Cytotoxicity of the cigarette extract on NHDF cells with or without treatment by the compound (Ia)

| Compounds tested | Cellular viability on NHDF (Optical density) |
|---|---|
| Control | 1.618 |
| Cigarette extract | 1.357 |
| Cigarette extract + (Ia) 10 ppm | 1.674 |

TABLE 12

Cytotoxicity of the cigarette extract on NHEK cells with or without treatment by the compound (Ia)

| Compounds tested | Cellular viability on NHEK (Optical density) |
|---|---|
| Control | 2.070 |
| Cigarette extract | 1.392 |
| Cigarette extract + (Ia) 10 ppm | 2.589 |

The analysis of the results obtained shows that the compound (Ia) maintains the cellular viability in the presence of cigarette extract (diluted to) 1/50°, which demonstrates the protective effect of this compound in a manner that is respectively highly (p<0.01) and very highly significant (p<0.001) on the NHEK and NHDF cells.

EXAMPLE 15

Effect of the Compound (Ia) According to the Invention on the Damage to the DNA (Double-Strand Breaks) Induced by a Cigarette Extract The cells used for this example are normal human Fibroblasts (NHDF) and normal human epidermal Keratinocytes (NHEK).

The cells are cultured at the concentration of 3000 cells per well of 96-well plates in the presence of standard culture medium for NHDF or NHEK (for 24 hours, 37° C., 5% $CO_2$).

After pretreatment of the cells with the compound (Ia) at 10 ppm for 24 hours, the cells are treated with the cigarette extract diluted to 1/50° with or without compound (Ia) at 10 ppm for 24 hours. The absorbance is read a first time at 450 nM (Multiskan®).

After washing, fixation in formalin and permeabilisation of the cells, the latter are incubated with antibodies targeting γ-H2AX (Millipore) and revealed by a secondary antibody (Invitrogen) bound to fluorescein for 45 min.

After washing, the samples are then placed in the presence of DAPI for 10 min in order to mark the nuclei, then rinsed once again. The marked proteins are observed and quantified with an automated fluorescence microscope (ArrayScan® (Cellomics®)). The cells treated by the compound (Ia) are then compared to the untreated cells or to the cells only exposed to the cigarette extract.

The results obtained are shown in tables 13 and 14 below.

TABLE 13

Double-strand breaks of the DNA induced by a cigarette extract in NHDF cells with or without treatment by the compound (Ia)

| Compounds tested | Double-strand breaks of the DNA for NHDF (AU) |
|---|---|
| Control | 6441 |
| Cigarette extract | 11404*** |
| Cigarette extract + (Ia) 10 ppm | 8752*** |

TABLE 14

Double-strand breaks of the DNA induced by a cigarette extract in NHEK cells with or without treatment by the compound (Ia) (***p < 0.001 and *p < 0.05, non-parametric Mann-Whitney test)

| Compounds tested | Double-strand breaks of the DNA for NHEK (AU) |
|---|---|
| Control | 10346 |
| Cigarette extract | 13269*** |
| Cigarette extract + (Ia) 10 ppm | 11193* |

The analysis of the results obtained shows that the compound (Ia) according to the invention is capable of neutralising the stress induced by the cigarette extract by reducing, in a significant manner, the quantity of γH2AX in NHDF and NHEK.

This study demonstrates the effectiveness of the compound (Ia) in protection against the stress induced by the extract of cigarettes by preventing or promoting the repair of the double damage to DNA. These results confirm the detoxifying and anti-ageing preventive agent action of the compound (Ia) according to the invention.

EXAMPLE 16

Effect on the Reduction of the Survival of Human Keratinocytes Induced by a Cigarette Extract, of the Compounds According to the Invention (Ia) and (Ib), and of Caffeic Acid as a Comparison This study aims to compare the protective or repairing effect of the compounds according to the invention (Ia) and (Ib) with respect to the damage induced on the skin by a cigarette extract. For comparison, caffeic acid (supplier: Acros) is also tested. This acid forms a basic unit of the compounds (Ia) and (Ib) according to the invention.

The NHEK cells are inoculated in a 96-well plate in a suitable medium (Promocell), at a rate of 9000 cells per well, and incubated 24 h at 37° C. and 5% carbon dioxide.

The compounds to be tested are prepared as follows:
(Ia): 10 mg of compound+909 μL of DMSO
(Ib): 7 mg of compound+636 μL of DMSO
caffeic acid: 10 mg of compound+909 μL of DMSO Each stock solution above is diluted 1000 times, to 10 ppm in the culture medium, then the solutions obtained are filtered by means of a nylon filter (0.22 μm). The final solutions are concentrated to 10 ppm in 0.1% DMSO.

Solutions at 20 ppm in 0.2% DMSO are also prepared in a similar manner, for dilution in the cigarette extract.

An extract of 20 cigarettes is prepared as indicated in example 14 above. This extract is then diluted to 1/50 in the culture medium; or to 2/50 in the culture medium, then to 1/2 in the culture medium, to which the compound to be tested is added at 20 ppm.

The cells are pretreated for 24 h with the compound to be tested at 10 ppm in the culture medium.

The cells are then treated with the cigarette extract diluted to 1/50$^{th}$ with or without the compound tested at 10 ppm for 24 h.

3 h before the end of the test, 10 μl of WST1 cellular proliferation reactant (Roche) are added into each well. The absorbance at 450 nm is measured before and after the addition of WST1 reactant, by means of a Multiskan® reader. The treated cells are compared to the untreated cells and to the cells exposed to the cigarette extract.

Figure 4:
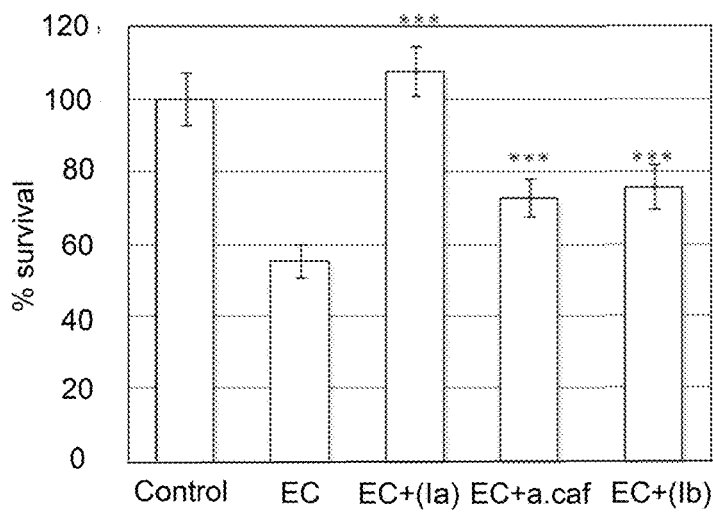
FIG. 4 shows a bar graph showing the percentage of survival of NHEK keratinocytes exposed for 24 h to a cigarette extract, alone (EC) or with pretreatment and treatment by compounds according to the invention (EC+(Ia), EC+(Ib)) or by caffeic acid (EC+a.caf), the Control designating cells not treated and not exposed to the cigarette extract.

The results obtained, in terms of % survival of the cells for each condition tested, are shown in FIG. 4. It is observed that the cigarette extract (EC) greatly reduces the survival percentage of the cells (up to 55% survival). Caffeic acid has a slight effect on the survival of the cells (73% survival). The compound (Ib) according to the invention also has a slight, but significant, effect of improvement of the survival of the cells (76% survival). As for the compound (Ia) according to the invention, it has a very strong effect of protection of the cells exposed to the cigarette extract (108% survival of the cells).

Thus, the compound (Ia) according to the invention totally protects the cells against the stress induced by the cigarette extract, and in particular, in a very surprising manner, much better than the caffeic acid which forms a unit of its structure.

EXAMPLE 17

Evaluation of the Protective Effectiveness of Compounds According to the Invention (Ia), (Ic) and (Id) and of Comparative Compounds Against UVAs on a Skin Explant Ex-Vivo The compound tested are the following:
compounds according to the invention (Ia), (Ic) and (Id),
caffeic acid,
pyridoxamine,
and comparative compound Comp.1, having the formula:

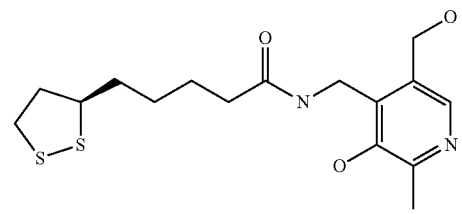 [SMILES: Cc1ncc(CO)c(CNC(=O)CCCC[C@@H]2CCSS2)c1O]

1/ Protocol 1.1/ Treatment of the Samples

The test was carried out on NativeSkin® skin explants (Genoskin), a biopsy of skin bathed in a solid, nourishing matrix while its epidermal surface is preserved in contact with the air. The biopsy is firmly anchored in the matrix and sealed in order to prevent any lateral diffusion of formulation intended for topical application.

The study was carried out on a donor 51 years old (phototype 2) under the following conditions.

The compounds tested are implemented in a composition containing them at 0.9 mmol/L in a mixture of Carbopol® (0.5% p/p), DMSO (0.1% p/p) and H$_2$O (qsp 100%).

The samples are irradiated at 60 J/cm$^2$ UVA every day for 3 days. A treatment is carried out for 24 h before the irradiation, by application of the composition tested onto the sample (deposition of 40 μl of composition onto the stratum corneum), then a post-treatment of 24 h after the irradiation, in the same manner.

A Control of the sample of skin non-irradiated and a Control of the sample of skin irradiated are also carried out, both with application of the vehicle alone (0.5% Carbopol®, 0.1% DMSO, H$_2$O). The Control of the non-irradiated sample of skin is introduced into the irradiator in a sheet of aluminium, in such a way as to protect it against UVs.

The samples are sampled, cut (according to the conventional method of cryo-sectioning implementing paraffin and freezing) and fixed in 1 ml of formalin for 24 h.

1.2/ Detection Method

The explants are then included in paraffin and sections of 5 μm are made.

The slides are then coloured with haematoxylin (basic compound marking the nuclei) and eosin (acidic compound marking the conjunctive tissue).

The slides obtained are also marked by immunohistochemistry with the biomarker γ-H2Ax.

The analysis of the marking is carried out with a DM5000B fluorescence microscope (Leica Microsystems) and 10 images are acquired for each sample.

1.3/ Analysis of the Data

For the marking with γ-H2Ax, for each image, the total number of nuclei is detected with 4',6-diamidino-2-phenylindole (dapi). In the same image, the number of nuclei having the marking is quantified. The ratio of the number of positive nuclei, multiplied by 100, to the number of total nuclei, is calculated, in order to obtain a percentage (=(positive nuclei*100)/total nuclei), n=10 per sample.

A statistical analysis is carried out with a student's test by comparing the samples to the control (p value<0.5*, p value<0.05, p value<0.005*, ns not significant).

2/ Histological Analysis

The images obtained by a fluorescence microscope are shown in FIG. 5.

As it can be seen in this drawing, the control sample (a) has a morphology of the conventional epidermis with the stratification of the keratinocytes into 4 cohesive layers.

The irradiated sample of skin (b) has a modification of the organisation of the layers of the epidermis and the appearance of pyknotic nuclei revealing a phenomenon of apoptosis. The phenotype of the irradiated sample is also found for the skins irradiated and treated with caffeic acid (c), pyridoxamine (d) and the comparative compound Comp.1 (h).

The skin appears to be partly protected with the compound (Id) according to the invention (g).

With the compounds (Ia) (e) and (Ic) (f) according to the invention, the morphology of the epidermis is identical to that of the non-irradiated control. The skin is totally protected from the deleterious effects of the UVAs.

3/ Analysis of the Breaks in the DNA

The images obtained by a fluorescence microscope after marking by the biomarker γ-H2AX are shown in FIG. 6.

Figure 7:
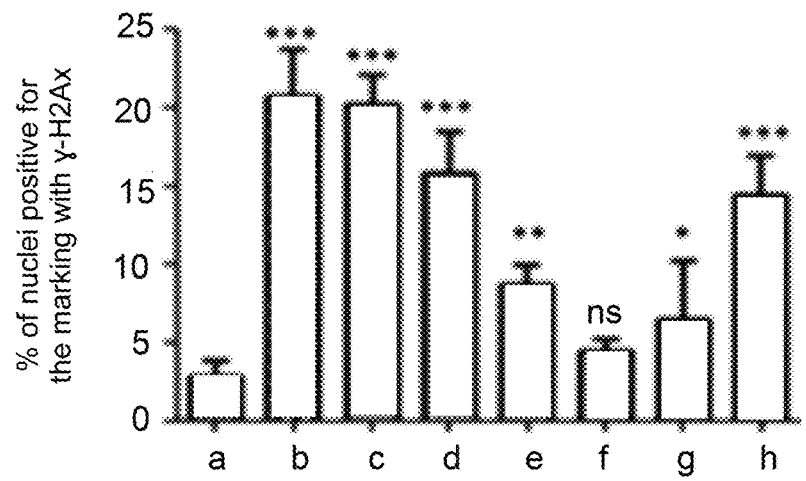
FIG. 7 shows a graph showing the percentage of nuclei positive for marking with γ-H2AX, quantified with respect to the total number of nuclei, for explants of skin respectively a/ non-irradiated untreated, b/ irradiated with UVAs untreated, c/ irradiated with UVAs treated with caffeic acid, d/ irradiated with UVAs treated with pyridoxamine, e/ irradiated with UVAs treated with the compound (Ia) according to the invention, f/ irradiated with UVAs treated with the compound (Ic) according to the invention, g/ irradiated with UVAs treated with the compound (Id) according to the invention, h/ irradiated with UVAs treated with the comparative compound Comp.1 (average over 10 samples for each condition).

The percentage of cells positive for the marking with γ-H2AX is calculated for each condition. The results obtained are shown in FIG. 7.

There, it can be observed that without treatment, repeated irradiation with the UVAs causes an increase of nuclei having the marking by, and thus of the number of nuclei having breaks in the DNA.

The skins treated with caffeic acid (c), pyridoxamine (d), and the comparative compound Comp.1 (h) have a level similar to the irradiated sample (b) (ns) and clearly increased with respect to the non-irradiated control (a) (*). As for the skins treated with the compounds according to the invention (Ia) (e) and (Id) (g), they have an increase in the percentage of cells having damage to the DNA in comparison with the control, but clearly reduced with respect to the irradiated control sample (b) (, ***, respectively). The skin treated with the compound (Ic) according to the invention (f) advantageously has the same phenotype as the non-irradiated control sample The compounds according to the invention (Ia), (Ic) and (Id) thus effectively protect the skin against UVAs and allow by that-itself to slow down the appearance of the symptoms of ageing of the skin.

As for the caffeic acid, the pyridoxamine and the compound Comp.1, they do not have any effect of protection of the skin against the UVAs.

It is clear from the above examples that the compounds according to the invention, and in particular the compound having the formula (Ia), and the compound having the formula (Ic), combine properties that allow them, applied topically onto the skin surface, to effectively combat external aggressions, in particular UV radiation and pollution, by both preventive and curative actions. These compounds act in particular on the antioxidant and anti-inflammatory defences of the skin, they inhibit the matrix metalloproteases and promote the repair of the DNA. The method for cosmetic treatment of the skin that implements them is thus particularly effective for the prevention and the repair of the signs of skin ageing.

EXAMPLES 18 to 24

Cosmetic Compositions

Cosmetic compositions according to the invention have the following compositions.

In these examples, the quantities of each ingredient are expressed in percentages by weight, with respect to the total weight of the composition.

EXAMPLE 18

Cosmetic Composition for a Detoxifying Soothing Treatment of the Eyes Contour

This cosmetic composition will be used 2 times per day, in the morning and evening, via circular application around the eyes.

TABLE 15

| Composition for a detoxifying soothing treatment of the contour of the eyes | |
|---|---|
| Ingredient | % |
| Water | 79.43 |
| Glycerine | 3.63 |
| Acrylates/C10-30 alkyl acrylate crosspolymer | 0.30 |
| Polyacrylate crosspolymer-6 | 0.30 |
| Sodium polyacrylate | 0.40 |
| Coco-caprylate/caprate | 3.00 |
| Isopropyl palmitate | 1.80 |
| Tridecyl trimellitate | 3.60 |
| Chlorphenesin | 0.30 |
| Benzyl alcohol (and) ethylhexylglycerine (and) tocopherol | 0.90 |
| Compound (Ia) | 0.50 |
| *Aloe barbadensis* leaf juice | 5.50 |
| Boron nitride | 0.30 |
| Sodium hydroxide | 0.04 |
| | 100.000 |

EXAMPLE 19

Cosmetic Composition for a Face Anti-Ageing Milk

This cosmetic composition will be used 2 to 3 times per day, in the morning and evening, via application onto the entire face except for mucosae.

TABLE 16

Face anti-ageing milk

| Ingredient | % |
| --- | --- |
| Water | 75.27 |
| Glycerine | 3.30 |
| Xanthan gum | 0.50 |
| Polysorbate 60 | 2.50 |
| Sorbitan stearate | 2.50 |
| Isononyl isononanoate | 1.50 |
| Ppg-3 benzyl ether ethylhexanoate | 2.00 |
| Phenyl trimethicone | 3.00 |
| Ethylhexyl cocoate | 2.00 |
| *Butyrospermum parkii* butter | 1.00 |
| Hydroxyethyl acrylate/sodium acryloyldimethyl taurate copolymer & isohexadecane & polysorbate 60 | 2.00 |
| Aluminium starch octenylsuccinate | 1.00 |
| Compound (Ia) | 0.10 |
| Hyaluronic acid | 2.00 |
| Perfume | 0.20 |
| Citric acid | 0.03 |
| Chlorphenesin | 0.30 |
| Phenoxyethanol | 0.30 |
| Ethylhexyl glycerine | 0.50 |
| | 100.00 |

EXAMPLE 20

Cosmetic Composition for a Face Detoxifying Lightening Care

This cosmetic composition will be used once per day, in the morning, via application onto the entire face except for the mucosae and the neck.

TABLE 17

Composition for a face detoxifying lightening care

| Ingredient | % |
| --- | --- |
| Water | 79.36 |
| Glycerine | 3.00 |
| Xanthan gum | 0.20 |
| Sodium polyacrylate | 0.25 |
| Cetyl alcohol (and) glyceryl stearate (and) peg-75 stearate (and) ceteth-20 (and) steareth-20 | 2.00 |
| Coco-caprylate/caprate | 5.00 |
| *Helianthus annuus* seed oil | 3.00 |
| C12-15 alkyl benzoate | 1.00 |
| Polyacrylamide (and) c13-14 isoparaffin (and) laureth-7 | 3.00 |
| Sodium acrylate/sodium acryloyldimethyl taurate copolymer/isohexadecane/polysorbate 80 | 0.74 |
| 3-o-ethyl ascorbic acid | 1.00 |
| Compound (Ia) | 0.20 |
| Perfume | 0.15 |
| Chlorphenesin | 0.30 |
| Phenoxyethanol | 0.30 |
| Ethylhexyl glycerine | 0.50 |
| | 100.00 |

EXAMPLE 21

Cosmetic Composition for an spf 25 Sunscreen—Face and Neck

This cosmetic composition will be used before and during exposure to the sun.

TABLE 18

SPF 25 sunscreen - Face and neck

| Ingredient | % |
| --- | --- |
| Water | 60.65 |
| Coco-caprylate/caprate | 4.00 |
| Butyl methoxydibenzoylmethane | 3.00 |
| Octocrylene | 10.00 |
| Homomenthyl salicylate | 5.00 |
| Benzophenone-3 | 3.00 |
| Dimethicone | 2.00 |
| Titanium dioxide (and) silica | 2.00 |
| Cetearyl alcohol (and) cetearyl glucoside | 3.00 |
| Arachidyl alcohol (and) behenyl alcohol (and) arachidyl glucoside | 2.00 |
| Xanthan gum | 1.00 |
| Tocopheryl acetate | 0.50 |
| Edeta B Powder | 0.05 |
| Chlorphenesin | 0.10 |
| Glycerine | 2.00 |
| Ethylhexyl glycerine | 0.20 |
| Phenoxyethanol | 0.30 |
| Perfume | 0.20 |
| Compound (Ia) | 2.00 |
| | 100.00 |

EXAMPLE 22

Cosmetic Composition for a Detoxifying Hydrating Anti-Ageing Face Care

This cosmetic composition will be used in the evening before sleep.

TABLE 19

Composition for a detoxifying hydrating anti-ageing face care

| Ingredient | % |
| --- | --- |
| Water | 67.55 |
| Glycerine | 3.00 |
| Chlorphenesin | 0.30 |
| Xanthan gum | 0.50 |
| Acrylates/c10-30 alkyl acrylate crosspolymer | 0.50 |
| Soda solution at 10% | 0.60 |
| Cetearyl alcohol (and) coco glucoside | 1.50 |
| Arachidyl alcohol (and) behenyl alcohol (and) arachidyl glucoside | 3.50 |
| *Shorea robusta* seed butter | 3.00 |
| Stearic acid | 2.00 |
| *Sesamum indicum* (sesame) seed oil | 1.50 |
| *Simmondsia chinensis* seed oil | 2.50 |
| *Helianthus annuus* seed oil | 3.50 |
| Propanediol | 4.50 |
| Dimethicone | 1.00 |
| Tocopheryl acetate | 0.50 |
| Phenoxyethanol | 0.30 |
| Ethylhexylglycerine | 0.50 |
| Perfume | 0.20 |
| Compound (Ia) | 0.05 |
| Hyaluronic acid | 2.00 |
| Resveratrol | 1.00 |
| | 100.00 |

EXAMPLE 23

Cosmetic Composition for a Detoxifying Aftershave

This cosmetic composition will be used for after shaving facial hair.

TABLE 20

| Detoxifying aftershave | |
|---|---|
| Ingredient | % |
| Water | 65.30 |
| Colourant - solution at 0.01% | 1.00 |
| Menthyl lactate | 0.50 |
| *Aloe barbadensis* leaf juice | 0.50 |
| Compound (Ia) | 2.00 |
| Phenoxyethanol | 0.30 |
| Chlorphenesin | 0.30 |
| Ethylhexylglycerine | 0.50 |
| Polyacrylate crosspolymer-6 | 1.60 |
| Peg-11 methyl ether dimethicone | 6.00 |
| Dimethicone | 1.00 |
| Glycerine | 3.00 |
| Ethanol | 7.00 |
| Water | 10.00 |
| Perfect skin | 0.30 |
| Ppg-26 buteth-26 (and) peg-40 hydrogenated castor oil | 0.70 |
| | 100.00 |

EXAMPLE 24

Cosmetic Composition for a Detoxifying Unified Tinted Cream

This cosmetic composition will be used as a foundation, preferably in the morning or during the day.

TABLE 21

| Detoxifying unified tinted cream | |
|---|---|
| Ingredient | % |
| Water | 60.400 |
| C14-22 alcohol (and) c12-20 glucoside | 2.500 |
| Dimethicone | 0.500 |
| C12-15 alkyl benzoate | 5.000 |
| Sodium acrylate/sodium acryloyldimethyl taurate copolymer/isohexadecane/polysorbate 80 | 3.500 |
| Dimethicone | 2.000 |
| Cyclopentasiloxane | 3.000 |
| Ci 77492 (and) glycerine (and) water (and) xanthan gum (and) sodium citrate | 0.830 |
| ci 77491 (and) glycerine (and) water (and) xanthan gum (and) sodium citrate | 0.860 |
| Ci 77499 (and) glycerine (and) water (and) xanthan gum (and) sodium citrate | 0.190 |
| Ci 77891 (and) glycerine (and) water (and) xanthan gum (and) sodium citrate | 19.200 |
| 3-o-ethyl ascorbic acid | 1.000 |
| Compound (Ia) | 0.200 |
| Ethylhexyl glycerine | 0.300 |
| Phenoxyethanol | 0.500 |
| Perfume | 0.020 |
| | 100.00 |

The invention claimed is:

1. Method for cosmetic treatment of the skin of an individual, comprising the administration, to said individual, of a composition containing, in a cosmetically acceptable vehicle, a compound having the general formula (I):

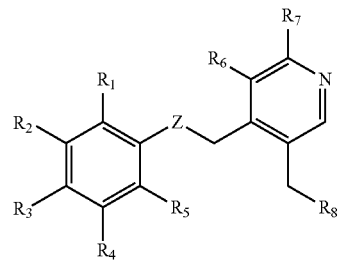

wherein:
$R_1$, $R_2$, $R_3$, $R_4$, $R_5$, $R_6$, $R_7$ and $R_8$, which may be identical or different, each represent a hydrogen atom, a halogen atom, a hydroxyl group, a linear or branched, saturated or unsaturated, C1-C16 hydrocarbon radical, or an —OR' radical in which R' represents a linear or branched, saturated or unsaturated, C1-C16 hydrocarbon radical,
at least one group out of $R_1$, $R_2$, $R_3$, $R_4$, $R_5$, $R_6$, $R_7$ and $R_8$ not representing a hydrogen atom or a halogen atom,
Z represents a covalent bond or a spacer arm,
or one of the salts thereof.

2. Method according to claim 1, wherein the administration of said composition to said individual is carried out by applying said composition topically onto the skin of said individual.

3. Method according to claim 1, wherein Z represents a spacer arm carrying an amide function.

4. Method according to claim 3, wherein Z represents a group having the formula (II):

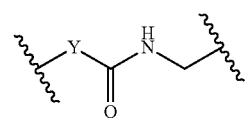

wherein Y represents a covalent bond or a linear or branched, saturated or unsaturated, C1-C16 hydrocarbon radical.

5. Method according to claim 4, wherein at least one out of $R_3$, $R_4$, $R_5$, $R_6$ and $R_8$ represents a hydroxyl group, and Y represents a covalent bond or a C2-C4 alkenyl radical.

6. Method according to claim 1, wherein said compound of general formula (I) has the formula (I'):

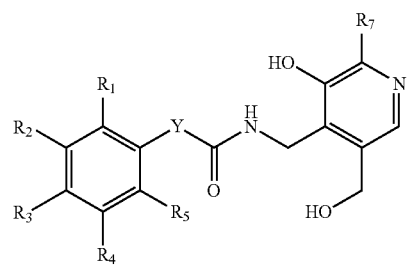

wherein
$R_1$, $R_2$, $R_3$, $R_4$, $R_5$ and $R_7$, which may be identical or different, each represent a hydrogen atom, a halogen atom, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one group out of $R_1$, $R_2$, $R_3$, $R_4$ and $R_5$ representing a hydroxyl group, and Y represents a covalent bond or a C2-C4 alkenyl radical.

7. Method according to claim 6, wherein, in the general formula (I'), at least $R_1$ and $R_2$ each represent a hydrogen atom.

8. Method according to claim 6, wherein, in the formula (I'), $R_3$ does not represent a hydrogen atom and $R_1$ and $R_5$ each represent a hydrogen atom.

9. Method according to claim 6, wherein, in the formula (I'), at least one substituent out of $R_2$, $R_3$ and $R_4$ represents a hydroxyl group.

10. Method according to claim 1, wherein said compound of general formula (I) has the formula (I"):

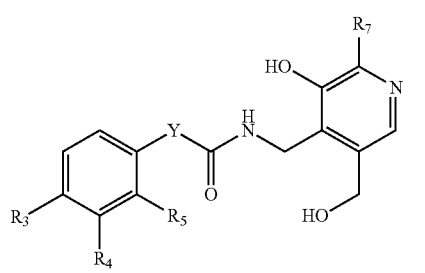

wherein $R_3$, $R_4$, $R_5$ each represent a hydrogen atom, a halogen atom, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one first group out of $R_3$, $R_4$ and $R_5$ representing a hydroxyl group and at least one second group out of $R_3$, $R_4$ and $R_5$ representing a hydroxyl group or an —OR' radical in which R' represents a linear or branched, saturated or unsaturated, C1-C4 hydrocarbon radical, $R_7$ represents a linear or branched, saturated or unsaturated, C1-C4 hydrocarbon radical, and Y represents a covalent bond or a C2-C4 alkenyl radical.

11. Method according to claim 10, wherein, in the formula (I"), $R_3$ does not represent a hydrogen atom and $R_5$ represents a hydrogen atom.

12. Method according to claim 10, wherein, in the formula (I"), at least one substituent out of $R_3$ and $R_4$ represents a hydroxyl group.

13. Method according to claim 1, wherein said compound of general formula (I) has the formula (I'''):

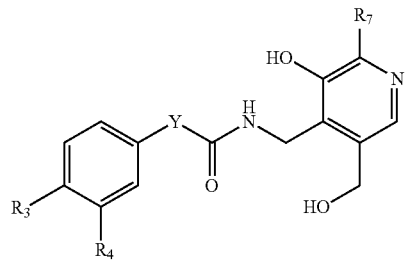

wherein $R_3$ represents a hydroxyl group, or an —OR' radical in which R' represents a linear or branched, saturated or unsaturated, C1-C16 hydrocarbon radical, $R_4$ represents a hydrogen atom or a hydroxyl group, $R_7$ represents a linear or branched, saturated or unsaturated, C1-C4 hydrocarbon radical, and Y represents a covalent bond or a C2-C4 alkenyl radical.

14. Method according to claim 13, wherein, in the formula (I'''), $R_4$ represents a hydroxyl group.

15. Method according to claim 1, wherein said compound of general formula (I) has the formula (Ia):

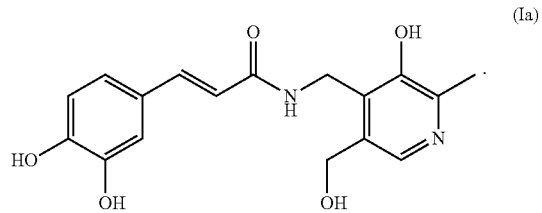

16. Method according to claim 1, wherein said compound of general formula (I) has the formula (Ic):

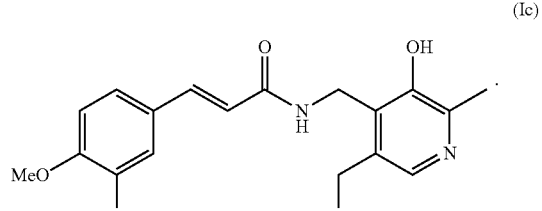

17. Cosmetic composition, containing a compound having the general formula (I), or one of the salts thereof, with the exclusion of the following compounds:

3-(2,4-dihydroxyphenyl)-N-(3-hydroxy-5-hydroxymethyl-2-methyl-pyridin-4-ylmethyl)-acrylamide 3-(3,5-dihydroxyphenyl)-N-(3-hydroxy-5-hydroxymethyl-2-methyl-pyridin-4-ylmethyl)-acrylamide 3-(2,6-dihydroxyphenyl)-N-(3-hydroxy-5-hydroxymethyl-2-methyl-pyridin-4-ylmethyl)-acrylamide, in a cosmetically acceptable vehicle:

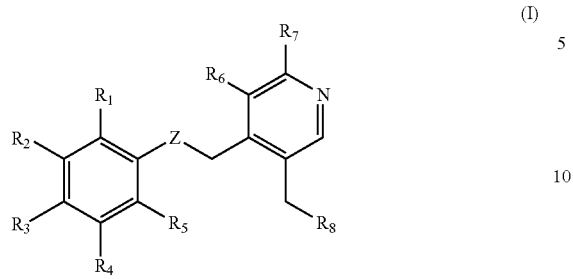

wherein:
$R_1$, $R_2$, $R_3$, $R_4$, $R_5$, $R_6$, $R_7$ and $R_8$, which may be identical or different, each represent a hydrogen atom, a halogen atom, a hydroxyl group, a linear or branched, saturated or unsaturated, C1-C16 hydrocarbon radical, or an —OR' radical in which R' represents a linear or branched, saturated or unsaturated, C1-C16 hydrocarbon radical, at least one group out of $R_1$, $R_2$, $R_3$, $R_4$, $R_5$, $R_6$, $R_7$ and $R_8$ not representing a hydrogen atom or a halogen atom, Z represents a covalent bond or a spacer arm.

\* \* \* \* \*